(12) United States Patent
Brik et al.

(10) Patent No.: US 12,251,168 B2
(45) Date of Patent: Mar. 18, 2025

(54) SYSTEMS, METHODS, AND DEVICES FOR LOCALIZED TRACKING OF A VERTEBRAL BODY OR OTHER ANATOMIC STRUCTURE

(71) Applicant: Medos International Sarl, Le Locle (CN)

(72) Inventors: Robert Brik, Cambridge, MA (US); Brice Dudley, Jr., Round Rock, TX (US); William Miller, Middleboro, MA (US); Marc Puls, Thörigen (CH); William Frasier, New Bedford, MA (US); Cheng-Ju Wu, Raynham, MA (US)

(73) Assignee: Medos International Sarl, Le Locle (CH)

( * ) Notice: Subject to any disclaimer, the term of this patent is extended or adjusted under 35 U.S.C. 154(b) by 846 days.

(21) Appl. No.: 17/334,308

(22) Filed: May 28, 2021

(65) Prior Publication Data

US 2022/0378511 A1     Dec. 1, 2022

(51) Int. Cl.
*A61B 34/20*     (2016.01)
*A61B 17/34*     (2006.01)
(Continued)

(52) U.S. Cl.
CPC .......... *A61B 34/20* (2016.02); *A61B 17/3421* (2013.01); *A61B 17/7074* (2013.01);
(Continued)

(58) Field of Classification Search
CPC ........ A61B 17/3421; A61B 2017/3454; A61B 34/20; A61B 2034/2046; A61B 2034/301; A61B 2034/2048; A61B 2034/2049
See application file for complete search history.

(56) References Cited

U.S. PATENT DOCUMENTS

| | | |
|---|---|---|
| 4,083,364 A | 4/1978 | Kelly et al. |
| 4,580,936 A | 4/1986 | Francis et al. |
| | (Continued) | |

FOREIGN PATENT DOCUMENTS

| | | | |
|---|---|---|---|
| KR | 101170594 B1 | 8/2012 | |
| WO | 2020130558 A2 | 6/2020 | |
| WO | WO-2020145821 A1 * | 7/2020 | ............. A61B 34/20 |

OTHER PUBLICATIONS

Hausmann et al., "Endoluminal Endosurgery: Rivet Application in Flexible Endoscopy", Gastro Endoscopy, vol. 64, No. 1, Munich, Germany, Jul. 1, 2006, pp. 101-103.

(Continued)

*Primary Examiner* — Boniface N Nganga
(74) *Attorney, Agent, or Firm* — Condo Roccia Koptiw LLP

(57) ABSTRACT

Systems, methods, and instruments for tracking localized movement of an anatomic structure at a surgical site are provided that can, for example, detect and identify movement of the anatomic structure not otherwise tracked by a global navigation system. One embodiment can include a cannula with a localized navigation sensor coupled to a distal end thereof. The cannula can be coupled to a robot arm and the localized navigation sensor can detect movement of an anatomic structure relative to the cannula. The localized navigation sensor can include one or more tines that selectively extend from the cannula to contact the anatomic structure. A controller can receive data from the localized navigation sensor and a global navigation system, and determine if movement detected by the localized navigation sensor is tracked by the global navigation system. Systems, methods, and instruments of the present disclosure can be used independently of a global navigation system.

20 Claims, 14 Drawing Sheets

(51) Int. Cl.
  *A61B 17/70*   (2006.01)
  *A61B 34/30*   (2016.01)
  *A61B 90/00*   (2016.01)
  *A61B 17/00*   (2006.01)
  *A61B 17/56*   (2006.01)

(52) U.S. Cl.
  CPC ..... *A61B 34/30* (2016.02); *A61B 2017/00119* (2013.01); *A61B 2017/564* (2013.01); *A61B 2034/2053* (2016.02); *A61B 2034/2055* (2016.02); *A61B 2034/2063* (2016.02); *A61B 2034/2072* (2016.02); *A61B 2090/064* (2016.02)

(56) References Cited

U.S. PATENT DOCUMENTS

| | | | |
|---|---|---|---|
| 4,973,301 A | 11/1990 | Nissenkorn | |
| 5,083,573 A | 1/1992 | Arms | |
| 5,203,773 A | 4/1993 | Green | |
| 5,257,975 A | 11/1993 | Foshee | |
| 5,322,501 A | 6/1994 | Mahmud-Durrani | |
| 5,518,498 A | 5/1996 | Lindenberg et al. | |
| 5,637,097 A | 6/1997 | Yoon | |
| 5,685,826 A | 11/1997 | Bonutti | |
| 5,741,282 A | 4/1998 | Anspach, III et al. | |
| 6,231,561 B1 | 5/2001 | Frazier et al. | |
| 6,312,446 B1 | 11/2001 | Huebsch et al. | |
| 6,328,727 B1 | 12/2001 | Frazier et al. | |
| 6,406,234 B2 | 6/2002 | Frigg | |
| 6,419,669 B1 | 7/2002 | Frazier et al. | |
| 6,436,088 B2 | 8/2002 | Frazier et al. | |
| 6,632,197 B2 | 10/2003 | Lyon | |
| 6,669,674 B1 | 12/2003 | Macoviak et al. | |
| 6,743,207 B2 | 6/2004 | Elbert et al. | |
| 6,746,472 B2 | 6/2004 | Frazier et al. | |
| 7,025,756 B2 | 4/2006 | Frazier et al. | |
| 7,186,238 B2 | 3/2007 | Elbert et al. | |
| 7,347,866 B2 | 3/2008 | Daignault et al. | |
| 7,452,363 B2 | 11/2008 | Ortiz | |
| 7,621,950 B1 | 11/2009 | Globerman et al. | |
| 7,625,392 B2 | 12/2009 | Coleman et al. | |
| 7,815,659 B2 | 10/2010 | Conlon et al. | |
| 8,469,963 B2 | 6/2013 | Shoham | |
| 10,646,280 B2 | 5/2020 | Crawford et al. | |
| 2001/0039436 A1 | 11/2001 | Frazier et al. | |
| 2004/0193114 A1 | 9/2004 | Elbert et al. | |
| 2005/0043759 A1 | 2/2005 | Chanduszko | |
| 2005/0070926 A1 | 3/2005 | Ortiz | |
| 2005/0228413 A1 | 10/2005 | Binmoeller et al. | |
| 2005/0273135 A1 | 12/2005 | Chanduszko et al. | |
| 2006/0084998 A1 | 4/2006 | Levy et al. | |
| 2006/0217748 A1 | 9/2006 | Ortiz | |
| 2006/0264986 A1 | 11/2006 | Park et al. | |
| 2007/0135803 A1 | 6/2007 | Belson | |
| 2009/0105733 A1 | 4/2009 | Coleman et al. | |
| 2012/0226315 A1 | 9/2012 | Altarac et al. | |
| 2012/0265071 A1* | 10/2012 | Berke | A61B 34/32 600/439 |
| 2015/0209056 A1 | 7/2015 | Shoham et al. | |
| 2019/0175289 A1 | 6/2019 | Verner et al. | |
| 2020/0046404 A1 | 2/2020 | Page et al. | |
| 2020/0222079 A1 | 7/2020 | Swaney et al. | |
| 2021/0077206 A1 | 3/2021 | Crawford et al. | |
| 2022/0054209 A1 | 2/2022 | Lim et al. | |

OTHER PUBLICATIONS

Powers et al., "Comparison of the Biomechanics and Histology of Two Soft-Tissue Fixators Composed of 8ioabsorable Copolymers", Journal of Biomedical Materials Research: An Official Journal of The Society for Biomaterials, The Japanese Society for Biomaterials, and The Australian Society for Biomaterials and the Korean Society for Biomaterials, vol. 58, No. 5, 2001, pp. 486-495.

* cited by examiner

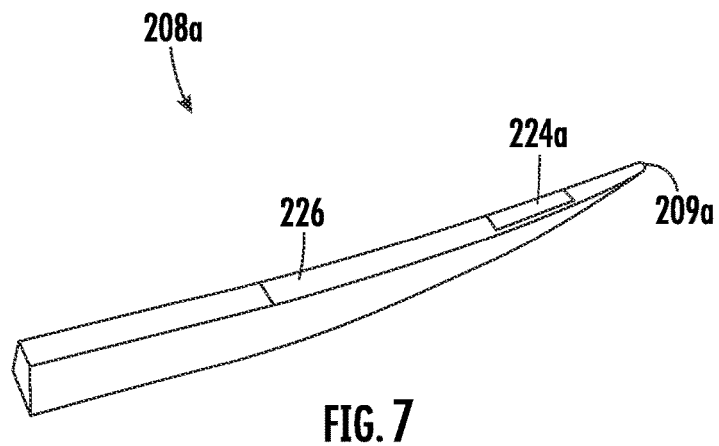
FIG. 7
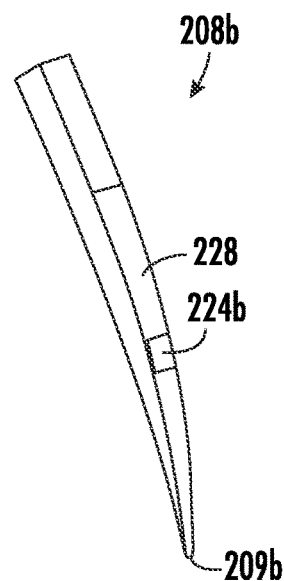
FIG. 8
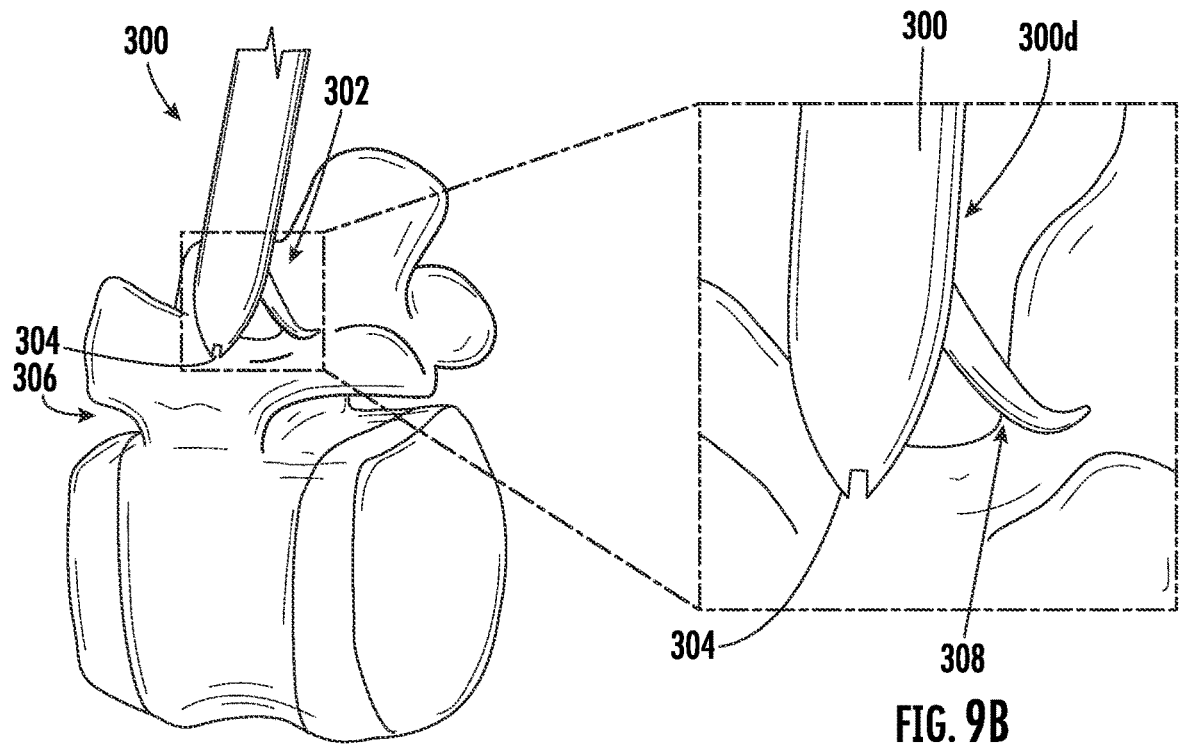
FIG. 9A
FIG. 9B

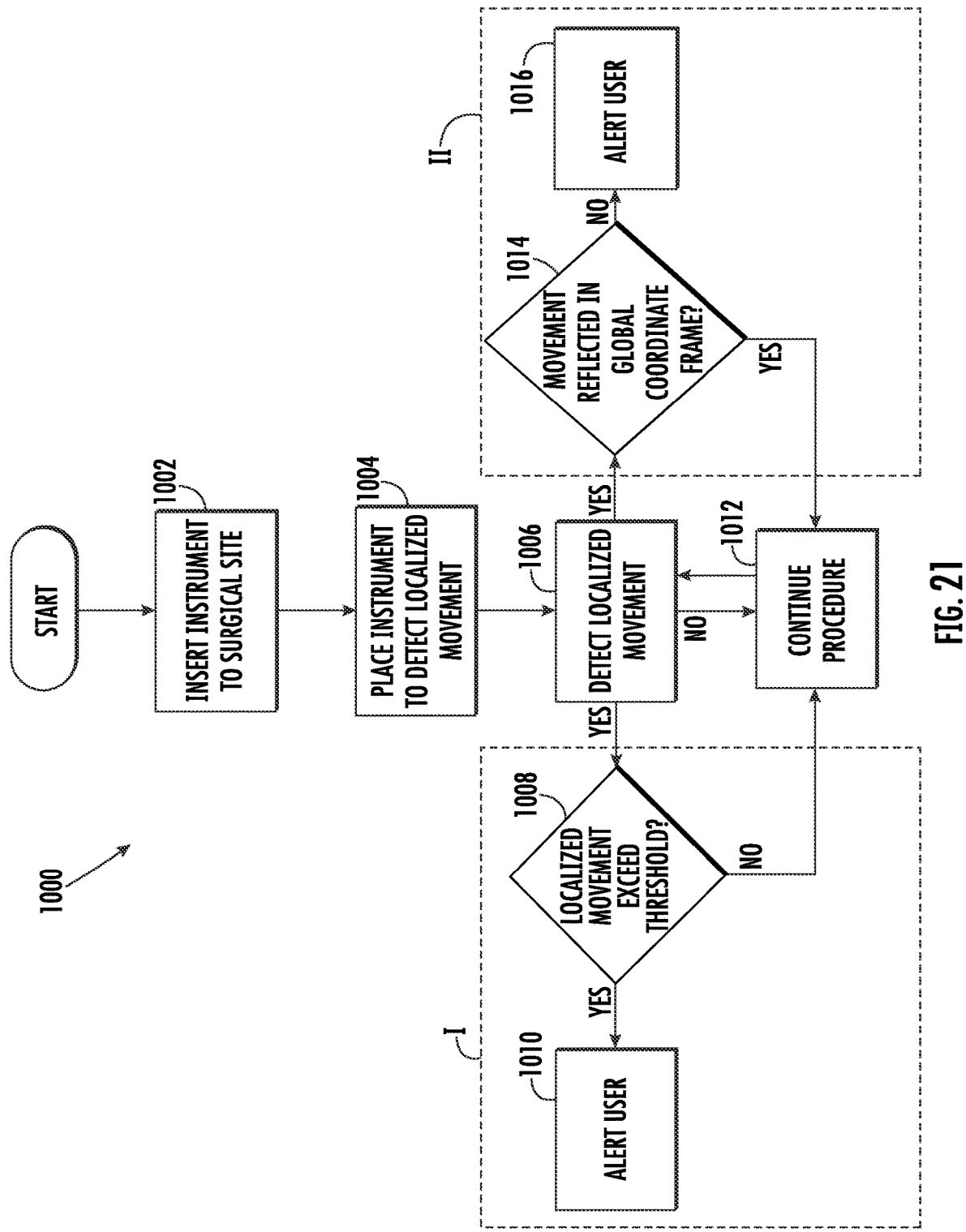

SYSTEMS, METHODS, AND DEVICES FOR LOCALIZED TRACKING OF A VERTEBRAL BODY OR OTHER ANATOMIC STRUCTURE

FIELD

The present disclosure relates to devices, systems, and methods for tracking localized movement of a vertebral body or other anatomic structure at surgical site which can, for example, identify inaccurate navigation of a global coordinate system and/or reduce the risk of skiving.

BACKGROUND

Many different surgical procedures utilize some form of surgical navigation or tracking to aid in positioning surgical instruments relative to portions of patient anatomy during a surgical procedure. In spinal surgery, for example, a surgical navigation system can be used during disc removal, bone drilling, implant insertion, e.g., screw and/or cage insertion, and other steps of the surgery. Surgical navigation can help surgeons avoid delicate neural or vascular structures when moving instruments at a surgical site. In a robotic or robot-assisted surgical procedure, surgical navigation can be important to correctly position a robotically controller or assisted surgical instrument relative to a patient.

There are a number of known surgical navigation or tracking technologies, including optical navigation or tracking systems that utilize, e.g., stereoscopic sensors to detect infra-red (IR) light reflected or emitted from one or more optical markers affixed to surgical instruments and/or portions of a patient's anatomy. By way of further example, a tracker having a unique constellation or geometric arrangement of reflective elements can be coupled to a surgical instrument or portion of patient anatomy and, once detected by stereoscopic sensors, the relative arrangement of the elements in the sensors' field of view, in combination with the known geometric arrangement of the elements, can allow the system to determine a three-dimensional position and orientation of the tracker and, as a result, the instrument or anatomy to which the tracker is coupled. The surgical navigation system can establish one or more coordinate frames based on different markers or reference points in relation to patient anatomy and/or landmarks in the operating environment (e.g., a surgical table, etc.), such that the surgical navigation system can track a position and orientation of the patient anatomy.

These systems, however, are not without drawbacks. One issue encountered with optical navigation or tracking systems is that one or more markers used to establish a patient reference frame are often removed from a location of the surgical site, e.g., to avoid crowding the surgical space, to prevent unintended jostling of the marker during surgery, etc. With continued reference to spinal procedures, for example, a surgical site may be located at a first vertebral level and a marker for establishing a patient reference frame may be coupled to bony structure several vertebral levels removed from the surgical site. As such, movement of patient anatomy at the surgical site, e.g., the vertebral body, may go undetected or unregistered by the optical navigation or tracking system. In other words, a position and/or orientation of patient anatomy at the surgical site runs the risk of being inaccurately reflected in the navigation or tracking system. This can lead to undesirable results, such as inaccurate or imprecise guiding of surgical instruments and/or surgical robot components, increased risk of skiving the patient anatomy at the surgical site, and misinformation communicated to a surgeon or other user regarding the surgical landscape.

Accordingly, there is a need for improved systems, methods, and devices that can monitor localized movement of patient anatomy at a surgical site and identify when such localized movement fails to be captured by a navigation or tracking system.

SUMMARY

Surgical systems, methods, and devices are disclosed herein that can detect movement of an anatomic structure at a surgical site relative to a cannula or instrument inserted into the surgical site, i.e., "localized" movement. The anatomic structure can be a bony anatomy that is not directly tracked by a global navigation system. For example, the anatomic structure can be a vertebral body that is one or more levels removed from a vertebral body or other structure to which a navigation marker is attached for monitoring by a global navigation system. In some embodiments, the present disclosure can determine whether detected localized movement of the anatomic structure is captured by a global navigation system. In this manner, the present disclosure can identify when placement and/or positioning of the anatomic structure at the surgical site may be inaccurately represented in the global navigation system, e.g., due to movement of the anatomic structure that may be minor or slight in nature. By capturing and alerting a user to such occurrences, remedial action can be taken to align the global navigation system and placement of the anatomic structure at the surgical site such that accurate navigation can be maintained, and a risk of skiving can be reduced. Additionally, or alternatively, embodiments of the present disclosure can detect localized movement of the anatomic structure and determine whether the detected localized movement exceeds a threshold condition. Accordingly, features of the present disclosure can be advantageously used in a variety of surgical procedures, e.g., with or without a global navigation system, minimally invasive procedures, robotic surgical procedures, robot-assisted surgical procedures, etc., to detect movement of patient anatomy at a surgical site that could otherwise go undetected and increase a risk of inaccurate navigation and/or skiving.

In one aspect, a surgical system includes a robot arm, a cannula coupled to the robot arm, a localized navigation sensor, and a controller. The localized navigation sensor is coupled to a distal end of the cannula and configured to detect movement of an anatomic structure relative to the cannula. The controller is configured to receive data from the localized navigation sensor and receive data from a global navigation system that tracks a location of a navigation marker located remotely from the anatomic structure. Further, the controller is configured to determine if movement of the anatomic structure detected by the localized navigation sensor is tracked by the global navigation system.

The localized navigation sensor can extend from the distal end of the cannula and, in some embodiments, can include at least one tine configured to extend from the distal end of the cannula. The controller can further be configured to determine movement of the anatomic structure based on a change in one or more of a geometry of the at least one tine and a location of the at least one tine. In some embodiments, the localized navigation sensor can include a plurality of tines configured to extend distally from the distal end of the cannula. In other embodiments, the localized navigation sensor can include at least one tine configured to extend radially from the distal end of the cannula.

The localized navigation sensor can include at least one of the following: a piezoelectric actuator, piezoelectric sensor, an ultrasound sensor, an electromagnetic sensor, a laser, a resistance-based sensor, a strain gauge. In some embodiments, the localized navigation sensor can be configured to detect a magnitude and a direction of localized movement of the anatomic structure. The anatomic structure can be a vertebral body.

In another aspect, a method includes positioning a cannula relative to an anatomic structure using a robot arm, detected movement of the anatomic structure relative to the cannula using a localized navigation sensor coupled to a distal end of the cannula, and determining if movement of the anatomic structure detected by the localized navigation sensor is tracked by a global navigation system that tracks a location of a navigation marker located remotely from the anatomic structure.

In some embodiments, the localized navigation sensor can include at least one tine and the method can further include extending the at least one tine from the distal end of the cannula to contact the anatomic structure. Detecting the movement of the anatomic structure can further include measuring at least one of a deformation in the tine or a change in location of the tine. In some embodiments, the method can include determining if movement of the anatomic structure exceeds a threshold amount of movement. The anatomic structure can be a vertebral body. In some embodiments, the method can further include alerting a user when the movement of the anatomic structure is not tracked by the global navigation system.

In another aspect, a surgical instrument includes a cannula and at least one sensor. The cannula has a proximal end and a distal end, the distal end configured for placement in proximity to an anatomic structure. The at least one sensor is configured to extend from the distal end of the cannula to contact the anatomic structure and measure localized movement of the anatomic structure relative to the cannula based on deformation of the at least one sensor.

The at least one sensor can include at least one tine configured to extend from the distal end of the cannula and, in some embodiments, the at least one tine can be configured to extend radially outward from the distal end of the cannula. In other embodiments, the at least one tine can include a plurality of tines configured to extend distally from the distal end of the cannula. The plurality of tines can be located circumferentially around the distal end oft cannula.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

FIG. 7 is a perspective view of another embodiment of a tine of the localized navigation sensor of FIG. 3;

FIG. 8 is a perspective view of another embodiment of a tine of the localized navigation sensor of the cannula of FIG. 3;

FIG. 9A an illustration of another embodiment of a cannula and a localized navigation sensor according to the present disclosure placed at a surgical site;

FIG. 9B is a detailed view of a distal end of the cannula and localized navigation sensor of FIG. 9A;

FIG. 21 is a flowchart of one embodiment of a method of monitoring localized movement of patient anatomy in a localized coordinate frame in accordance with the present disclosure.

DETAILED DESCRIPTION

Figure 1:
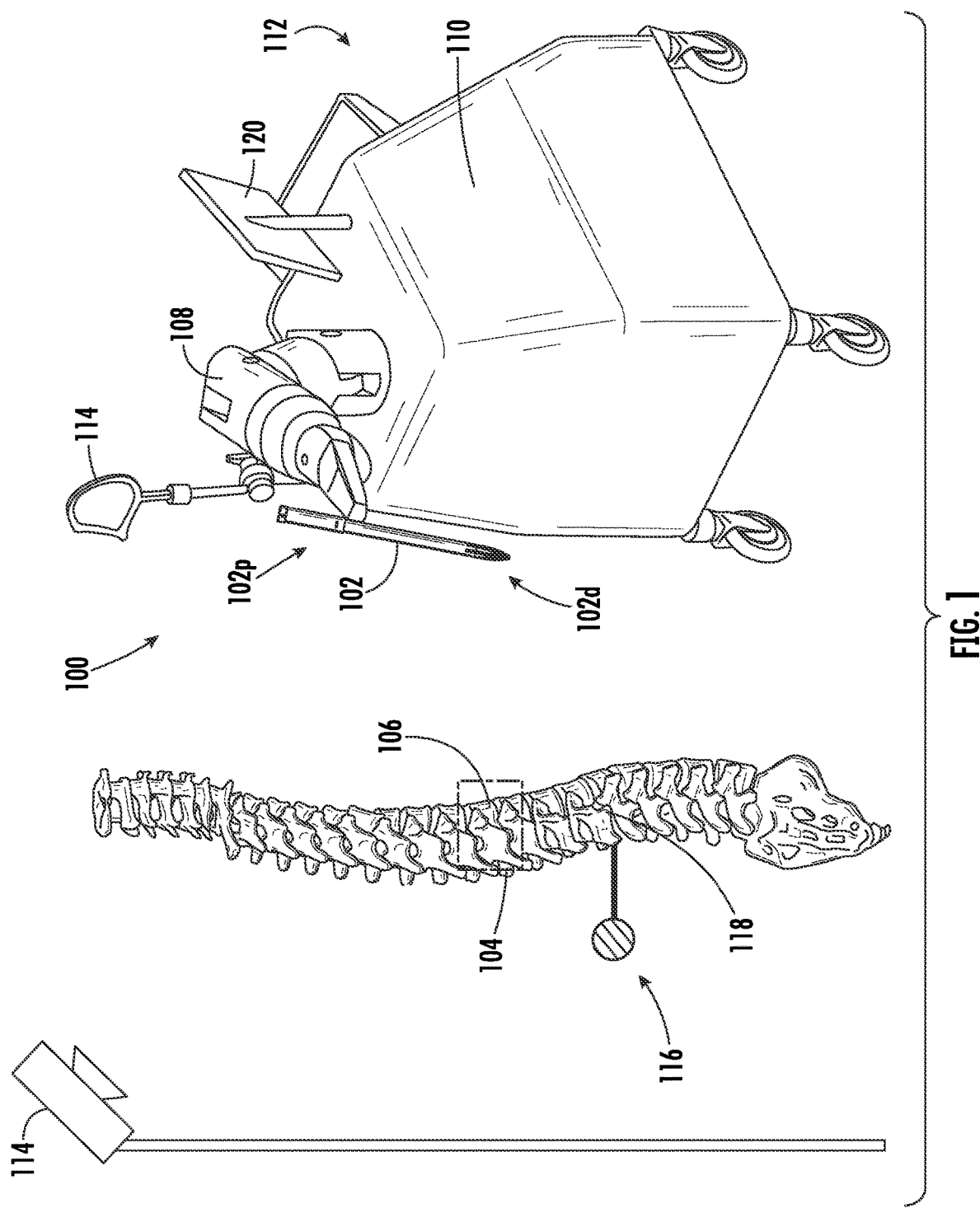
FIG. 1 is an illustration of a surgical system according to the present disclosure.

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. Equivalents to such linear and circular dimensions can be determined for different geometric shapes. Further, sizes and shapes of the devices, and the components thereof, can depend at least on the anatomy of the subject in which the devices will be used, the size and shape of objects with which the devices will be used, and the methods and procedures in which the devices will be used. To the extent features, sides, components, steps, or the like are described as being "first," "second," "third," etc. such numerical ordering is generally arbitrary, and thus such numbering can be interchangeable.

Localized movement detection systems and related methods are disclosed herein that can track localized movement of an anatomic structure and can alert a user when the detected localized movement goes unrecognized by a global navigation system and/or when the detected localized movement exceeds a threshold condition. Alerting a user to either or both such instances can identify movement of patient anatomy at the surgical site that could otherwise go undetected and negatively impact a surgical procedure, e.g., due to an increased skiving risk as a result of shifted patient anatomy, inaccuracies in a global navigation system coordinate frame, etc. Localized movement detection systems of the present disclosure can include a localized navigation sensor coupled to a cannula, or other surgical instrument, that can be advanced at a surgical site such that the cannula is in contact with, or adjacent to, an anatomic structure of the patient. The localized navigation sensor can detect and measure movement of the patient anatomy relative to the cannula. More particularly, the localized navigation sensor can collect and transmit data to a controller that can be used to identify movement of the anatomic structure relative to the cannula. In some embodiments, the controller can identify a magnitude and/or direction of the detected localized movement and can decouple the data to identify the mode(s) in which such movement occurs. As noted above, in some embodiments, localized motion detection systems of the present disclosures can be used in connection with a global navigation system and can alert a user when the localized movement detected by the localized navigation sensor is undetected or unregistered by the global navigation system, however features of the systems and methods disclosed herein can be advantageously utilized independently of a global navigation system. Moreover, the localized movement detection systems can be used during a procedure carried out by a surgical robot, a procedure carried out by a user, e.g., a surgeon, with some degree of robotic assistance, or in a procedure without involvement of surgical robots or robotic assistance.

FIG. 1 illustrates one embodiment of a surgical system 100 of the present disclosure that can detect localized movement of an anatomic structure at a surgical site. The system 100 can include a cannula 102 with a localized navigation sensor coupled thereto (not shown in FIG. 1, but better seen in subsequent figures and described in connection with the same, e.g., the localized navigation sensor 204 of FIG. 3). The cannula 102 can be advanced into a surgical site 104 such that a distal end 102d of the cannula is placed in contact with, or adjacent to, an anatomic structure, e.g., a vertebral body 106. With the cannula 102 in such a position, the localized navigation sensor can detect movement of the vertebral body 106 relative to the cannula 102. Relative movement between the vertebral body 106 and the cannula 102 can be referred to herein as "localized movement." In some embodiments, a proximal end 102p of the cannula 102 can be coupled to a robotic device, e.g., a robot arm 108 that can navigate the cannula and/or hold the cannula steady.

Localized navigation sensors of the present disclosure can collect data during a surgical procedure while the distal end 102d of the cannula 102 is in proximity to the vertebral body 106 that can be analyzed to detect localized movement of the anatomic structure (such data may be generally referred to herein as "sensory data"). The localized navigation sensor can transmit sensory data to a controller 110, which, in the illustrated embodiment of FIG. 1 can be included in a control unit cart 112 of the robot arm 108. The controller 110 can also receive data from a global navigation system that can include a stereoscopic sensor 114 and at least one reference marker 116. The reference marker 116 can consist of one or more tracking elements, e.g., reflective or active markers, and can be coupled to patient anatomy at a location remote from the surgical site 104 and, more particularly, removed from the vertebra 106 at the surgical site. For example, the marker 116 can be coupled to a vertebra 118 located one or more levels away from the surgical site 104. The stereoscopic sensor 114 can detect light reflected off of the reference marker 116 (e.g., reflected infra-red light in some embodiments) and can transmit data to the controller 110, which can utilize known fixed geometric positions of the tracking elements of the reference marker 116 and the detected positions of the tracking elements to determine a precise three-dimensional position and orientation of the reference marker 116 and thus the patient anatomy coupled thereto. In some embodiments, the global navigation system can include a second reference marker (not shown) that can, for example, be coupled to the control unit cart 112, robotic arm 108, or an end effector coupled to the robotic arm to locate the position of the cart and/or robot arm.

Data can be transmitted between components (e.g., the localized navigation sensor, the global navigation system, the robot arm 108, the controller 110, etc.) via any suitable connection, e.g., with wires (see FIGS. 4A and 4C) or wirelessly using a low latency transfer protocol. The controller 110 can carry out real-time control algorithms at a reasonably high frequency with low additional latency, e.g., to analyze data received from the localized navigation sensor, communicate data to a user, coordinate movement of the robotic arm 108, etc. As referenced above, the controller 110 can establish a global coordinate system based on information received from the global navigation system. More particularly, a position of the reference marker 116 can be used to track a position of the vertebra 118 to which it is coupled, which can establish a position of patient anatomy. However, as the surgical site 104 is located a distance away from the reference marker 116, movement of patient anatomy, i.e., the vertebra 106, at the surgical site can go undetected by the global navigation system. As will be described in detail below, in some embodiments, the controller 110 can receive data from the localized navigation sensor with respect to localized movement of the anatomic structure 106 and can determine whether the detected localized movement is tracked or registered in the global navigation coordinate system. Additionally or alternatively, the controller 110 can determine whether the detected localized movement exceeds a threshold condition. In some embodiments, the controller 110 can be in communication with a display 120 such that information from the controller can be visually communicated to a user via the display. For example, the controller 110 can alert a user if detected localized movement exceeds the threshold condition and/or if detected localized movement is not tracked by the global navigation system. In some embodiments, a visual alert or warning sign can be shown on the display 120 to alert a user to such conditions. By way of further example, the display 120 can show a three-dimensional rendering of patient anatomy, the surgical site, tracked components, etc.

Figure 2:
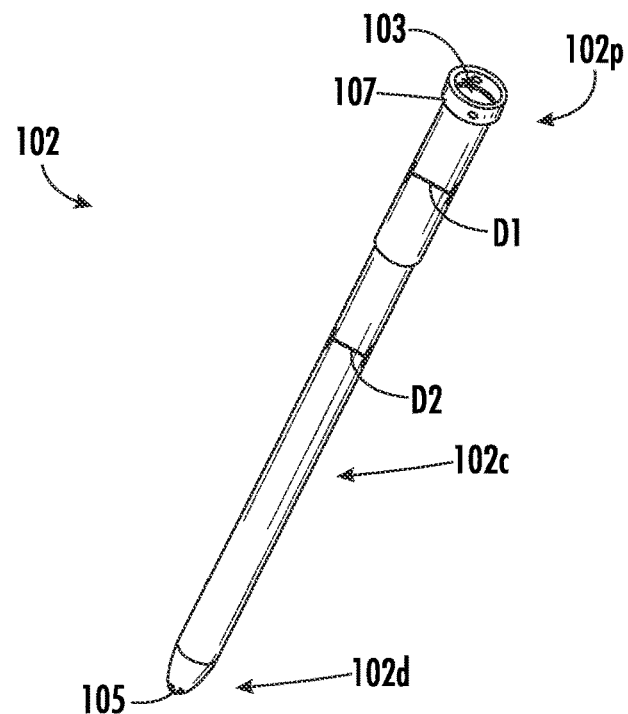
FIG. 2 is a perspective view of one embodiment of a cannula according to the present disclosure that can be used with the surgical system of FIG. 1.

FIG. 2 is a detailed view of the cannula 102 illustrated in FIG. 1 in connection with the surgical system 100. The cannula 102 can have a generally tubular body with an inner lumen 103 extending from the proximal end 102p to the distal end 102d of the cannula. As noted above, in some embodiments, the proximal end 102p of the cannula can be coupled to the robot arm 108 such the robot arm can control, in whole or in part, movement or placement of the cannula. In other embodiments, a user can manipulate the cannula 102 without assistance from the robot arm 108 or other surgical robot device. The proximal end 102p of the cannula 102 can have an enlarged diameter D1 relative to a diameter D2 of a central portion 102c of the cannula. A collar 107 can be formed at the proximal end 102p of the cannula 102 which can, in some embodiments, facilitate coupling of the cannula to the robot arm 108. The distal end 102d can have a generally conical shape which can taper from the central portion 102c of the cannula to a distal tip 105. As can be better seen in later figures, the distal tip 105 can include a plurality of teeth (e.g., teeth 304 in FIGS. 9A and 9B) that can grip or bite into an anatomic structure (e.g., vertebra 106) and provide stabilization of the cannula 102 relative to the anatomic structure.

The cannula 102 illustrated in FIG. 2 is one embodiment of a cannula according to the present disclosure, i.e., a cannula that can have a localized navigation sensor coupled thereto such that, with the cannula located in proximity to an anatomic structure at a surgical site, the localized navigation sensor can detect movement of the anatomic structure relative to the cannula. Various embodiments of localized navigation sensors of the present disclosure are described in greater detail below. For example, a localized navigation sensor can include one or more of a resistance-based sensor to detect force and/or displacement, a strain gauge, an ultrasound transducer, a laser, an electromagnetic tracker, a piezoelectric actuator, a piezoelectric sensor, or combinations thereof. Further, in some embodiments, a localized navigation sensor can include a fiber optic cable and/or camera(s) that can provide visualization of the anatomic structure. For example, a fiber optic cable can extend through the cannula 102 to the distal end 102d and/or camera(s) can be coupled to the distal end of the cannula, such that the surrounding surgical site, including the vertebra 106, can be imaged. In some embodiments, a localized navigation sensor can include multiple cameras, which can enable three-dimensional visualization of the anatomic structure and surgical site.

FIGS. 3-9B illustrate further embodiments of cannulas and localized navigation sensors that can be used in the surgical system of FIG. 1. The localized navigation sensors of these embodiments can include one or more tines that can selectively extend from a distal end of the cannula to contact an anatomic structure and detect localized movement of the anatomic structure relative to the cannula. In embodiments having a plurality of tines, the tines may be extended from the distal end of the cannula independently from one another or in unison with one or more other tines. Depending on the surrounding anatomic structure, in some instances, extending the tines, or a subset of tines, independently can aid in conforming the tines to the anatomic structure.

Figure 3:
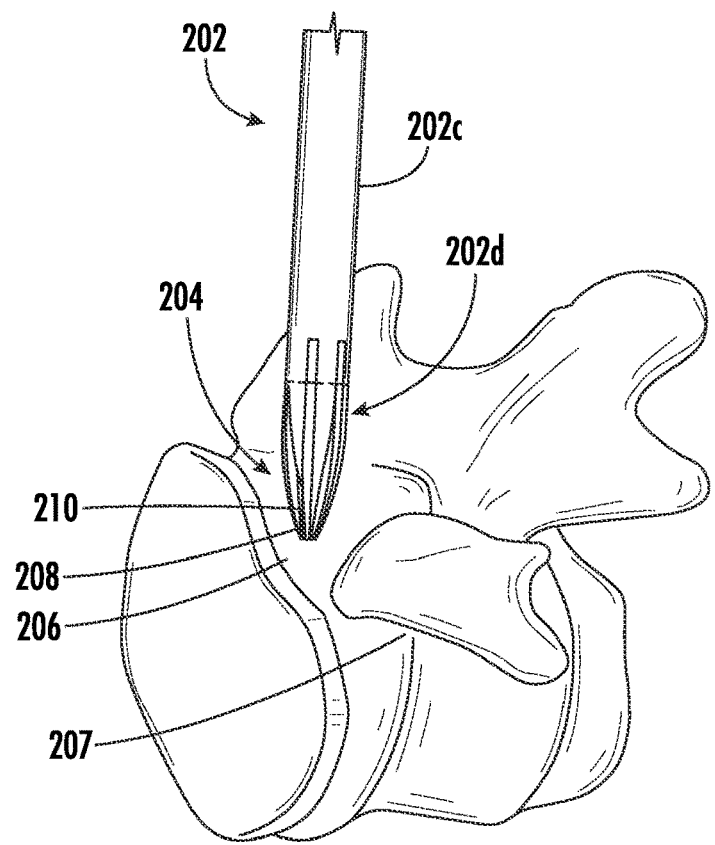
FIG. 3 is an illustration of another embodiment of a cannula and a localized navigation sensor according to the present disclosure placed at a surgical site.

FIG. 3 shows one embodiment of a cannula 202 with a localized navigation sensor 204 coupled thereto. The cannula can be inserted into a surgical site such that a distal end 202d of the cannula 202 is in proximity to an anatomic structure, e.g., vertebra 206. While not shown, a proximal end of the cannula 202 can be similar or identical to the proximal end 102p of the cannula 102 described above in connection with FIG. 2. A lumen 203 (see FIG. 4B) can extend from the proximal end to the distal end 202d of the cannula 202. The localized navigation sensor 204 can be coupled to the distal end 202d of the cannula and can detect and measure movement of the vertebral body 206 relative to the cannula 202. The localized navigation sensor 204 can include a plurality of tines 208 that can move longitudinally relative to the cannula 202 such that the tines 208 can extend distally past a distal tip 210 of the cannula 202 to contact the vertebral body 206, as shown in FIG. 3. In some embodiments, the plurality of tines 208 can bite into the vertebral body 206. Upon localized movement of the vertebral body 206, one or more of the plurality of tines 208 can undergo a change in tine geometry and/or location. The localized navigation sensor 204 can collect data related to the same and transmit the data to a controller, e.g., the controller 110 of FIG. 1, such that the localized movement can be detected and analyzed. While the illustrated embodiment of FIG. 3 shows the cannula 202 placed such that the tines 208 contact a surface of the vertebral body 206, alternative positioning of the cannula relative to the vertebra is within the scope of the present disclosure. For example, the cannula 202 can be placed at the surgical site such that the tines 208 can extend distally from the cannula to contact a surface of a pedicle 207 of the vertebral body.

Figure 4A:
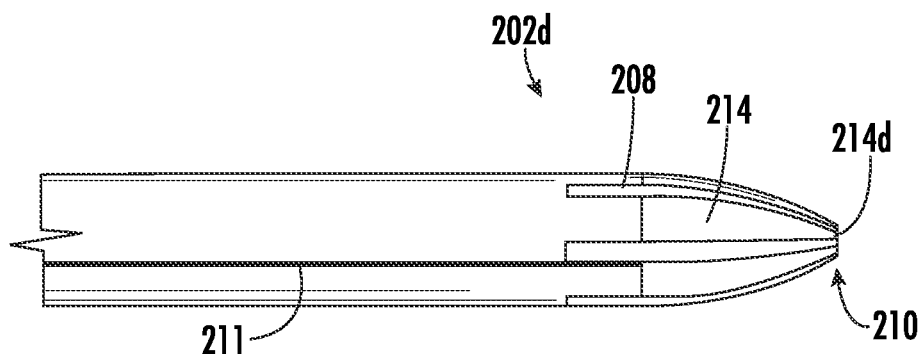
FIG. 4A is a side view of the cannula and localized navigation sensor of FIG. 3, with the localized navigation sensor in a first position.
Figure 4B:
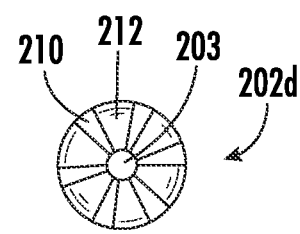
FIG. 4B is a bottom view of the cannula and localized navigation sensor of FIG. 3.
Figure 4C:
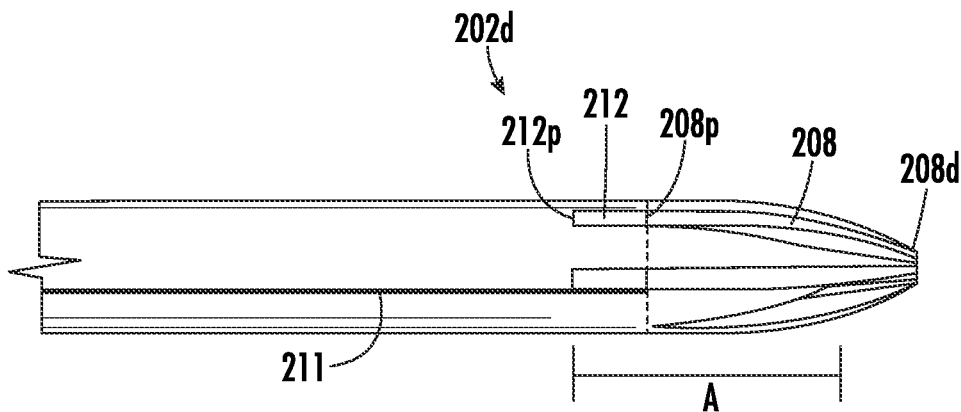
FIG. 4C is a side view of the cannula and localized navigation sensor of FIG. 3, with the localized navigation sensor in a second position.

FIGS. 4A-4C show the cannula 202 and the localized navigation sensor 204 of FIG. 3 in greater detail. The plurality of tines 208 of the sensor 204 can move between a first position in which the tines can be retracted within the cannula (see FIG. 4A) and a second position in which the tines can extend longitudinally from the cannula (see FIG. 4C). With reference to FIGS. 4A-4C, the distal end 202d of the cannula 202 can include a plurality of recesses 212 spaced apart along a circumference of the cannula body. In some embodiments, each recess 212 can be a slot that extends proximally from the distal tip 210 of the cannula 202 along a longitudinal axis of the cannula and can terminate at a location on the distal end 202d of the cannula a distance A from the distal tip. A tooth 214 can be formed between adjacent recesses 212 such that the distal tip 210 of the cannula 202 can have a plurality of spaced apart teeth.

A tine 208 can be received in one or more of the recesses 212. By way of example, six recesses 212 can be formed in the distal end 202d of the cannula 202 and can be spaced evenly or otherwise along a circumference of the cannula, with a tine 208 received within each recess. While six tines 208 arranged in the illustrated configuration of FIGS. 4A-4C can provide certain benefits, e.g., decoupling modes of localized movement, a greater or fewer number of tines and/or varying spacing between each tine in an even or unevenly distributed manner can be utilized in localized navigation sensors without departing from the spirit of the present disclosure. In the first position, e.g., as shown in FIG. 4A, a proximal end 208p of each tine 208 can be abut a proximal end 212p of the respective recess 212 and a distal end 208d of each tine can be flush with a distal end 214d of respective adjacent teeth 214 such that the distal end 210 of the cannula has a substantially continuous outer surface. As used herein, "outer surface" can refer to a surface facing away from the inner lumen of the cannula 202. The tines 208 can be sized and shaped such that, in the first position, an outer surface of each tine 208 can lie flush with an outer surface of the adjacent teeth 214.

FIG. 4C shows the cannula 202 with the localized navigation sensor 204 in the second position, in which the tines 208 can extend distally beyond the distal tip 210 of the cannula. More particularly, the tines 208 can be actuated from the first position (see FIG. 4A) such that the tines 208 move distally relative to the cannula 202 to extend distally from each tine's respect recess 212. The tines 208 can be extended until the distal tip 208d of the tines 208 contact the vertebral body 206, such that the tines can engage with or bite into the vertebral body. The tines 208 can be formed from a sturdy deformable material, e.g., an elastic metallic material, such that the tine may exhibit a deflection or deformation response to movement of the vertebral body 206.

In use, the cannula 202 can be inserted into a surgical site (see 104 in FIG. 1) with the tines 208 in the first position (see FIG. 4A), i.e., retracted into the recesses 212 of the cannula. The tines 208 can be extended distally (see FIG. 4C) beyond the distal tip 210 of the cannula 202 such that the tines 208 contact the vertebral body 206 at the surgical site (see FIG. 3). One or more of the tines 208 can include a sensing element that can collect data which can be analyzed to detect and identify relative movement of the anatomic structure. In some embodiments, each of the tines 208 can include a sensing element, while in other embodiments only a subset of the tines 208 can include a sensing element. The remaining tines can be non-sensing tines, which can provide benefit to the overall design and function of the cannula 202, e.g., as structural support.

FIGS. 5-8 illustrate various embodiments of tines 208 that can be used in accordance with the localized navigation sensor 204 described above with respect to FIGS. 3-4C. As introduced above, the tine 208 can include a sensing element such that, when the tine is in contact with patient anatomy, one or more of a geometry of the tine, position of the tine, and orientation of the tine can change in response to movement of the patient anatomy. The tine 208 can collect data associated with such change(s) and the localized navigation sensor can transmit the data to a controller 110 (see FIG. 1) for analysis.

Figure 5A:
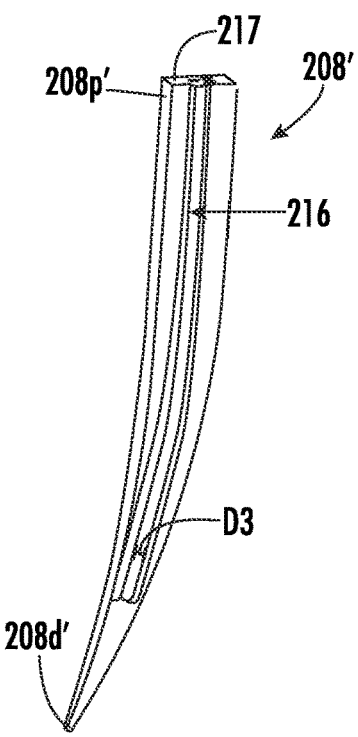
FIG. 5A is a partially-transparent perspective view of one embodiment of a tine of the localized navigation sensor of FIG. 3.
Figure 5B:
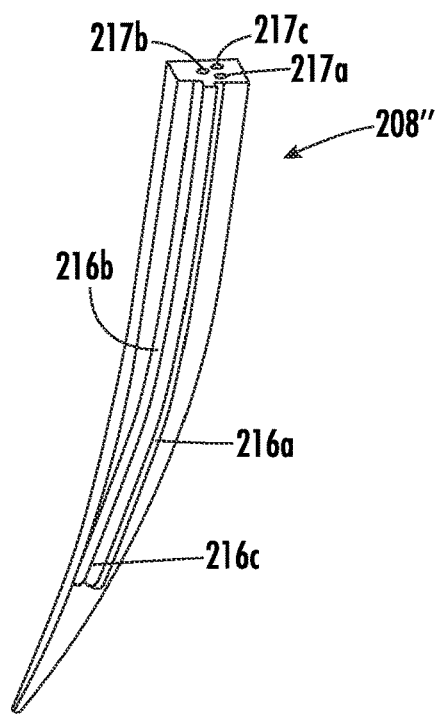
FIG. 5B is a partially-transparent perspective view of another embodiment of a tine of the localized navigation sensor of FIG. 3.
Figure 6:
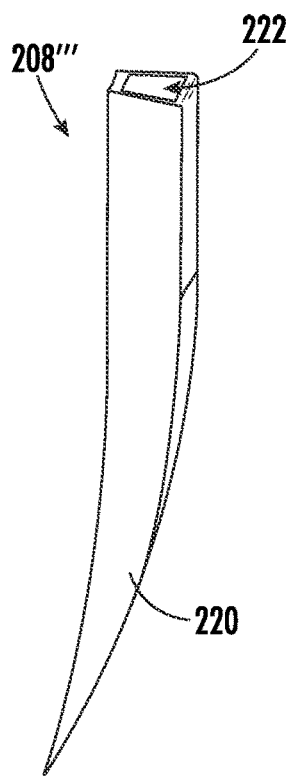
FIG. 6 shows a perspective view, a partially transparent perspective view, and a cut-away perspective view of another embodiment of a tine of the localized navigation sensor of FIG. 3.
Figure 6:
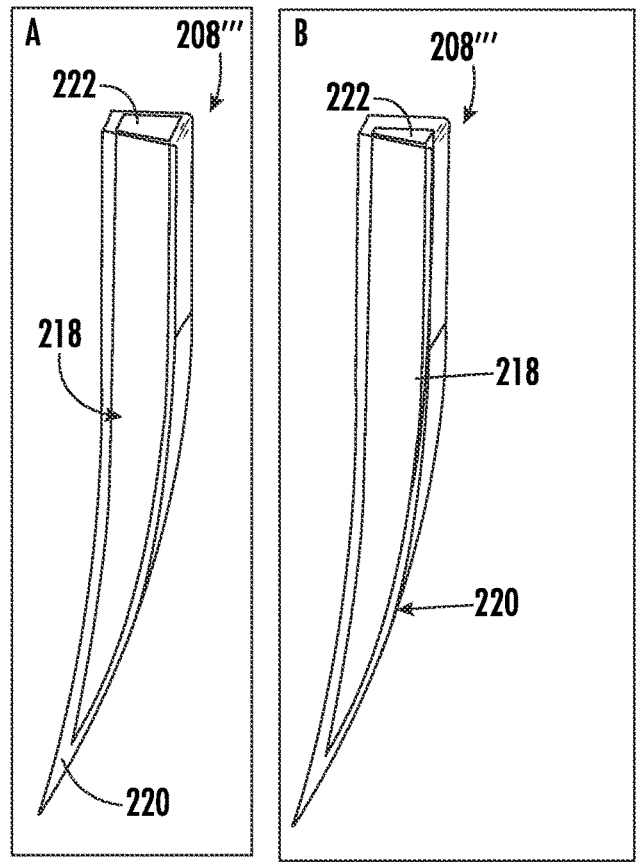

FIGS. 5A-6 illustrate various embodiments of tines 208', 208", 208''' of the present disclosure that can include a resistance-based sensor or a resistive element therein. For example, as shown in FIGS. 5A and 5B, in some embodiments tines 208', 208" can include one or more resistive element channels 216, 216a, 216b, 216c that can extend through a body of the tine and measure resistance to detect force and/or displacement. A resistance measured by the resistive element channels 216, 216a, 216b, 216c of a particular tine 208', 208" can correlate to an amount of bending that particular tine undergoes at the time. In some embodiments, a tine 208' can include a single resistive channel 216 extending from a proximal end of the tine 208p' towards a distal tip 208d' of the tine (see FIG. 5A). The resistive channel 216 can extend substantially centrally through the tine 208', although other placements of the channel are possible. In another embodiment, as shown in FIG. 5B, a tine 208" can include three resistive channels 216a, 216b, 216c, that can extend through the body of the tine. In some such embodiments, the three resistive channels 216a, 216b, 216c can be placed in a triangular configuration and substantially centrally located within the tine. The multiple resistive channels 216a, 216b, 216c contained within the single tine 208" can provide for a precise measurement of a direction of bending of the tine, as the resistance measurements from each of the three resistive channels can be analyzed and decoupled from one another. The resistive channels 216, 216a, 216b, 216c can be formed from a resistive piece of material or a filament extending through the interior of the tine 208', 208". By way of non-limiting example, each resistive channel 216, 216a, 216b, 216c can have a diameter D3 (see FIG. 5A) of about 0.3 mm to about 0.6 mm. The particular configuration, number of resistive channels, length of resistive channel, and/or diameter of resistive channel, can be determined based on, among other things, size of the tine 208', 208" and a desired sensor response. The resistive element channels 216, 216a, 216b, 216c can have an exposed face 217, 217a, 217b, 217c at the proximal end 208p', 208p" of the tine 208', 208", which can serve as a connection for signal transmission from the tine 208', 208" to the controller 110 (see FIG. 1).

FIG. 6 illustrates another embodiment of a tine 208''' with a resistive element 218 that can measure an amount of bending in the tine. A body 220 of the tine 208''' can be a non-conductive elastomer. The resistive element 218 can be formed by doping an interior portion of the body 220 with a conductive metal, such that the resistive element 218 forms a core within the body 220. This can be seen in inserts A and B of FIG. 6, which show the tine 208''' with a partially transparent body 220 and a partially cut-away body 220, respectively. A proximal face 220 of the resistive element 218 can be exposed at a proximal end 208p''' of the tine 208''', which can serve as an electrical connection for signal transmission between the tine 208''' and the controller 110 (see FIG. 1).

FIGS. 7 and 8 illustrate alternative embodiments of a tine 208a, 208b that can include at least one strain gauge 224a, 224b placed on or within the tine. The strain gauge(s) 224a, 224b can measure deformation of and/or pressure changes on the tine 208a, 208b. In some embodiments, the strain gauge 224a, 224b can be embedded directly into the tine 208a, 208b, while in other embodiments the strain gauge can be bonded to, or otherwise securely attached to, a surface of the tine 208a, 208b. FIG. 7 illustrates one embodiment in which the strain gauge 224a can be placed on an inner surface 226 of the tine 208a. As used herein, "inner surface" can refer to a surface facing towards the lumen 203 (see FIG. 3) of the cannula 202. In other embodiments, either additionally, or alternatively, the strain gauge 224b can be placed on an outer surface 228 of the tine 208b, as shown in FIG. 8. For a tine with an arcuate structure, the inner surface 226 can be concave and the outer surface 228 can be convex. The strain gauge 224a, 224b can be placed towards a distal tip 209a, 209b of the tine 208a, 208b, to the extent that the geometry of the tine and the gauge allow. Exact placement of the strain gauge 224a, 224b can be a function of tine geometry and/or strain gauge width. Size, shape, and placement of the strain gauge(s) 224a, 224b can vary based on, among other things, the dimensions of the tine 208a, 208b and desired sensitivity of the measurements. For example, in some embodiments a strain gauge can have an elongaterectangular configuration, such as the strain gauge 224a of FIG. 7, while in other embodiments a strain gauge can have a more square-shaped configuration, such as the strain gauge 224b in FIG. 8. One example of a strain gauge that can be used in accordance with the present disclosure is a Vishay General Purpose Linear Pattern Strain Gage that can be about 2.54 mm by about 0.51 mm by about 0.025 mm.

While the embodiments illustrated in FIGS. 7 and 8 show a single strain gauge 224a, 224b coupled to a tine 208a, 208b, in some embodiments, an array of strain gauge sensors can be placed along an inner and/or outer surface of the tine, which can enable increased precision sensing and lead to a better understanding of localized movement of the patient anatomy. As discussed in detail with reference to FIGS. 19-21, in some embodiments, an array of strain gauge sensors can be placed on the tine such that the sensor signals can be decoupled from one another and the various individual modes of localized movement, e.g., lateral translation, longitudinal translation, rotation, can be distinctly identified.

One or more conductive paths or wires (e.g., wire 211 in FIGS. 4A and 4C) can connect to the electrical connection of the resistance-based sensors/resistive elements 216, 216a, 216b, 216c, 218 or strain sensors 224a, 224b, described above. More particularly, the wire(s) 211 can extend along an interior or exterior of the cannula 202 to transmit the signals from the sensing elements of the localized sensor 204 to the controller 110 (FIG. 1). While only a single wire 211 in connection with a single tine 208 is illustrated in 4C, each tine of the localized navigation sensor 204 that includes a sensing element can have a connection to the controller 110 for transmitting data. Alternatively, transmission of data from the localized sensor 204 to the controller 110 can be done, in whole or in part, via a wireless connection. In instances in which the cannula 202 and localized navigation sensor 204 are utilized with the robot arm 108 (FIG. 1), the conductive path or wire 211 can extend to an end effector of the robot arm, which can process data from the localized sensor 204, e.g., with a printed circuit board (PCB) integrated within the end effector or robot arm, or further transmit the signals to a connected controller through a wired or wireless transmission. During manufacture, the localized navigation sensor 204 can be calibrated by determining the correlation between a reading of the resistance-based sensor(s)/resistive element(s) 216, 216a, 216b, 216c, 218 and/or strain gauge(s) 224a, 224b of a particular tine and deflection or deformation of the tine. The resulting calibration values can be encoded, e.g., in a chip onboard the cannula 202 (which can be in the same electronics package as the conductive wires 211), via a quick response (QR) code or bar code on cannula packaging, etc., and retrieved prior to or during a surgical procedure for signal processing.

FIGS. 9A and 9B illustrate another embodiment of a cannula 300 with a localized navigation sensor 302 coupled thereto in accordance with the present disclosure. FIG. 9A shows the cannula 300 located at a surgical site 104 (see FIG. 1) such that a distal tip 304 of the cannula can contact a vertebral body 306, or other anatomic structure. Contact between the distal tip 304 and the vertebral body 306 can stabilize the cannula 300 within the surgical site. The localized navigation sensor 302 can include at least one tine 308 that can extend radially outward from a distal end 300d of the cannula. More particularly, the tine 308 can extend outwardly from the cannula 300 and can contact the vertebral body 306 at a location that is remote from a location of contact between the distal tip 304 of the cannula and the vertebral body. The tine 308 can include one or more of the sensing elements described above in connection with FIGS. 5A-8 such that the tine and more broadly, the localized navigation sensor 302, can collect data with respect to a geometry, position, location, etc. of the tine that can be used to detect localized movement of the vertebral body 306. For example, bending of the tine 308 can indicate a change or shift in a direction of movement of the vertebral body 306 relative to the cannula 300. Deflection of the tine 308 can measure force of localized movement of the anatomy 306. In some embodiments, a plurality of tines 308 can extend radially outward from the cannula 300, with each tine configured to contact the vertebral body 306 at a location remote from the distal tip 304 of the cannula. Each of the plurality of tines 308 can include a sensing element, which can provide increased data with respect to detecting and identifying a direction and/or magnitude of localized movement.

Figure 10:
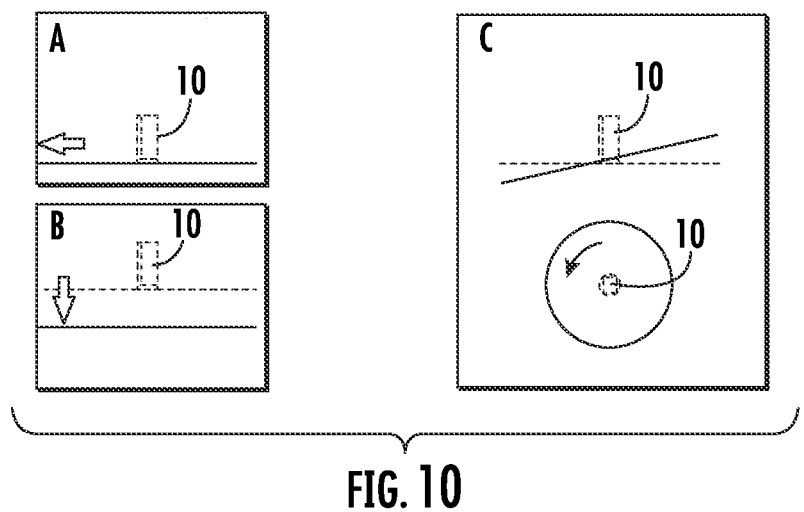
FIG. 10 is a diagram of various modes of movement of an anatomic structure.

As discussed above, localized navigation sensors 204, 302 of the present disclosure can be configured such that signals received by the controller 110 from the localized navigation sensors can be decoupled, which can lead to a precise determination of localized movement mode, magnitude, and direction of the vertebra 206, 306, or other anatomic structure. Decoupling sensor signals can be beneficial as the anatomic structure can move relative to the cannula in three different modes, simultaneously. Namely, and with reference to FIG. 10 which schematically illustrates the various modes of motion, an anatomic structure 10 can translate laterally (schematically illustrated in box A), translate longitudinally (schematically illustrated in box B), and rotate (schematically illustrated in box C) to varying degrees at the same time, such that a simple measurement reading from a localized navigation sensor may not always be sufficient to fully capture localized movement. By decoupling the signal(s) received from the localized navigation sensor 204, 304, the controller 110 of the present disclosure can identify each of the three modes of movement described above independently of one another. In this manner, localized movement of the patient anatomy relative to the cannula can be accurately and precisely measured and tracked.

Figure 11:
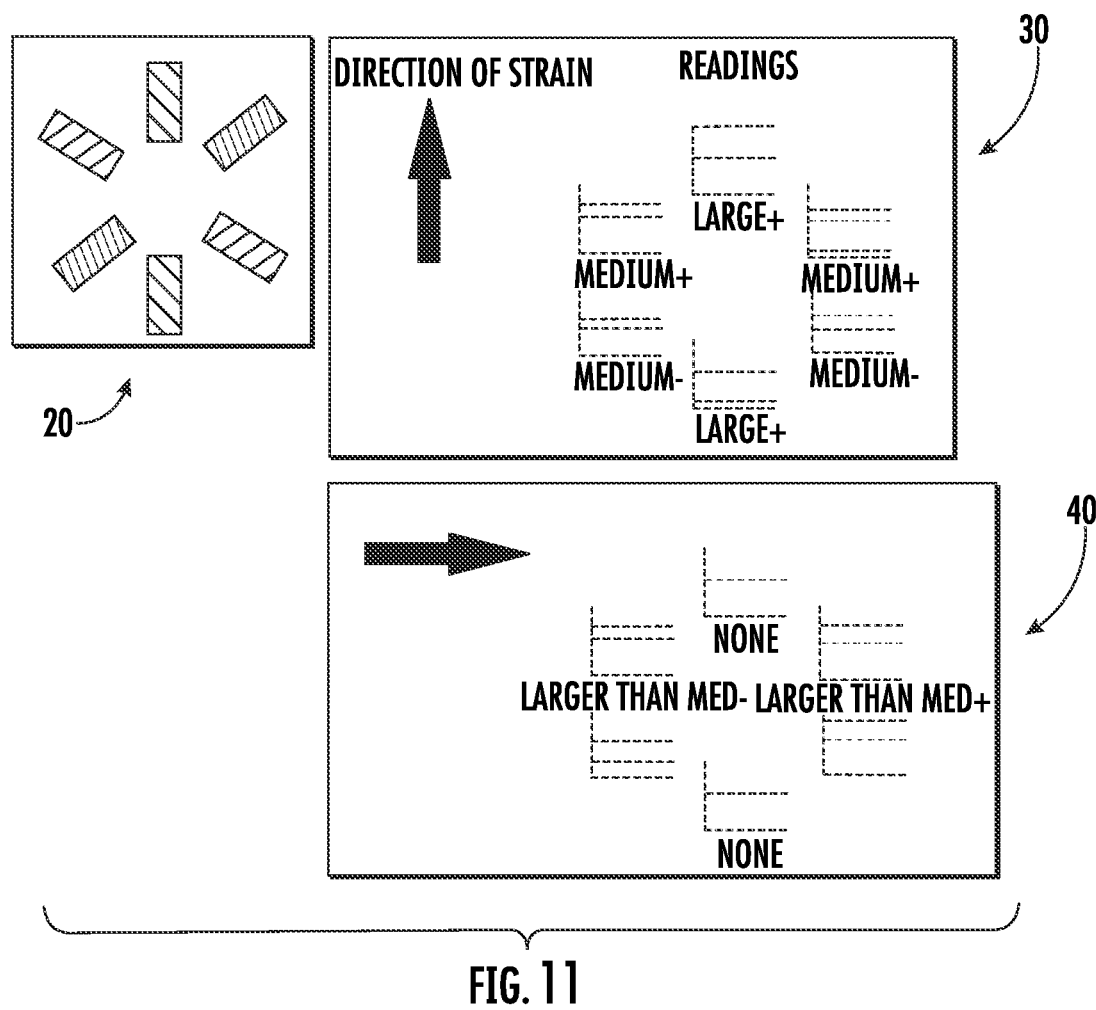
FIG. 11 is a diagram of one embodiment of a decoupling data framework that can be applied by a controller of the surgical system of FIG. 1.

In some embodiments, a statistical model can be programmed into the controller 110 to read and decouple the signals received from the localized navigation sensor 204, 304. In other embodiments, analytical decoupling can be performed. More particularly, and with reference to FIG. 11, a localized navigation sensor of the present disclosure can include six tines 208, 308, placed in the configuration 20 of FIG. 11, i.e., spaced equidistant around a circumference of a cannula 202, 300 such that three pairs of opposed sensors are formed. As noted above, localized navigation sensors and instruments in accordance with the present disclosure may have an alternative number and/or spacing of tines (e.g., with even or uneven spacing of tines). By way of example, such an analytical decoupling of data from tines in such a configuration can be analytically akin to a strain gauge rosette. Each of the six tines 208, 308 can include resistance-based sensors/resistive elements 216, 216a, 216b, 216c, 218 or strain sensors 224a, 224b. With the tines 208, 308 in such a configuration, the signal transmissions from each tine can be read and analyzed to identify the composite movement by magnitude and direction of strain and shear. For example, the controller 110 can identify a magnitude and direction of longitudinal strain by analyzing components of the data transmitted by each tine as shown in the sensor response diagram 30. Similarly, the controller 110 can identify a magnitude and direction of lateral strain by analyzing components of the data transmitted by each tine as shown in the sensor response diagram 40. By process of elimination, remaining components of the data transmitted by each tine can be attributed to shear.

Figure 12:
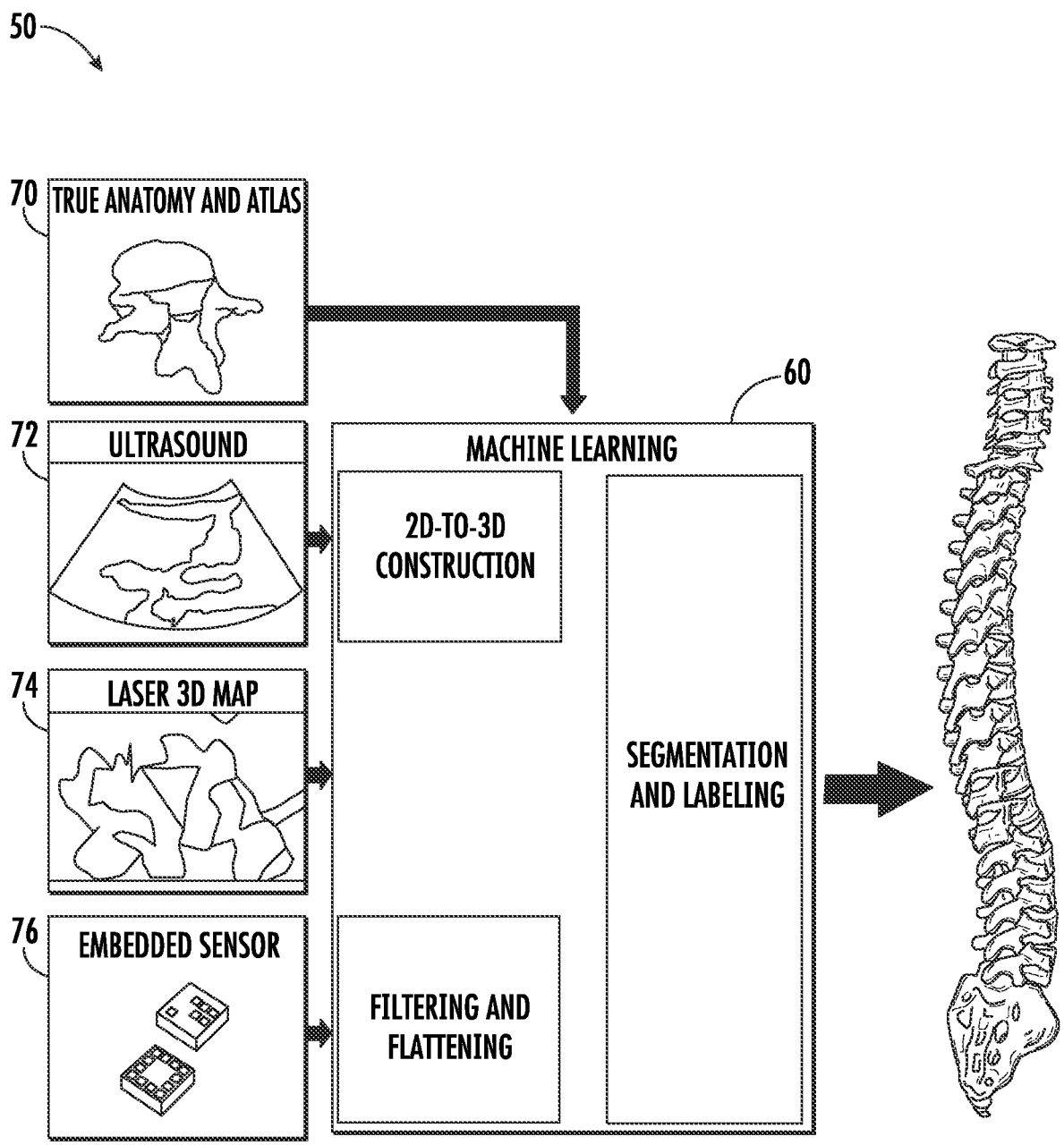
FIG. 12 is a diagram of another embodiment of a data analysis framework that can be applied by a controller of the surgical system of FIG. 1.

In instances or applications in which a signal from the localized navigation sensor cannot be easily decoupled, higher techniques of signal processing can be deployed to capture and identify precise localized movement of the patient anatomy at interest. For example, multimodal machine learning techniques can be applied to enhance movement detection and measurement. FIG. 12 schematically illustrates one embodiment of a multimodal machine learning system 50 that can be utilized by the controller 110 (see FIG. 1) of the present disclosure to process signals received from the localized navigation sensor. For example, the controller 110 can include a machine learning module 60 that can build a framework through which data from the localized sensor 204, 302 can be interpreted such that localized movement mode(s) and respective magnitude(s) can be determined. The machine learning module 60 can receive as input pre-programed information 70 pertaining to anatomy at the surgical site 104 (see FIG. 1). The pre-programed information 70 can include generic anatomic information and/or patient-specific information. The machine learning module 60 can receive as further inputs data from various pre-operative or intra-operative tests or scans related to the patient's anatomy at the surgical site, such as, for example, ultrasound data 72, three-dimensional maps 74, and/or data from sensors embedded in surgical instruments 76. The machine learning module 60 can take these inputs 70, 72, 74, 76 and construct three-dimensional models of anatomy at the surgical site, filter and flatten the signals, and segment and label the data to build a framework understanding of the surgical site anatomy. The controller 110 can then apply the machine learning framework 60 to signals received from the localized navigation sensors 204, 302 to understand and capture precise localized movement based on the localized navigation sensor data.

FIGS. 13-19 illustrate alternative embodiments of cannulas and localized navigation sensors in accordance with the present disclosure. As with the embodiments described above, the cannulas and localized navigation sensors of FIGS. 13-19 can be used in conjunction with a global navigation system during a surgical procedure, e.g., as part of the surgical system 100 of FIG. 1 or can be used during a surgical procedure independent of a global navigation system. Further, in some embodiments, the cannulas of FIGS. 13-19 can be coupled to a surgical robot, e.g. robot arm 108, such that the robot can control or assist with control of the cannula and/or localized navigation sensors.

Figure 13:
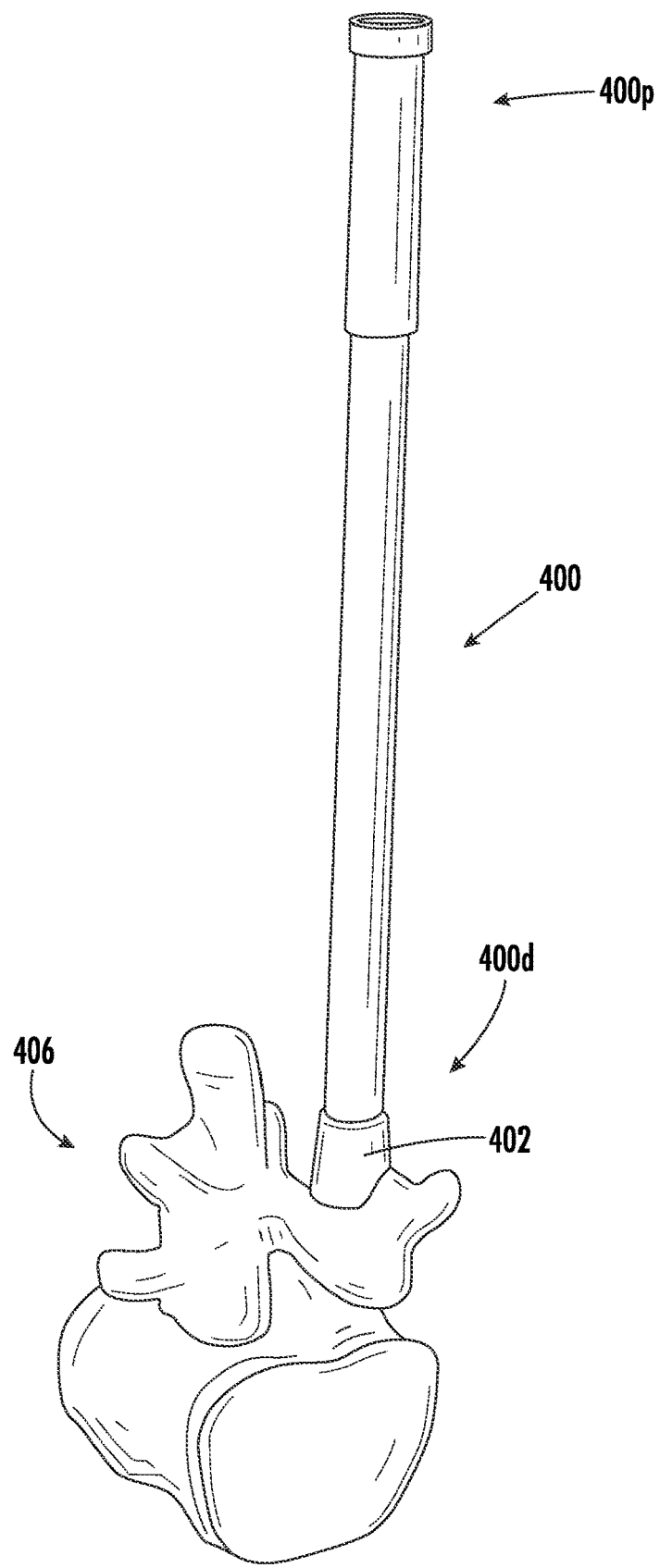
FIG. 13 is an illustration of another embodiment of a cannula and a localized navigation sensor according to the present disclosure placed at a surgical site.
Figure 14:
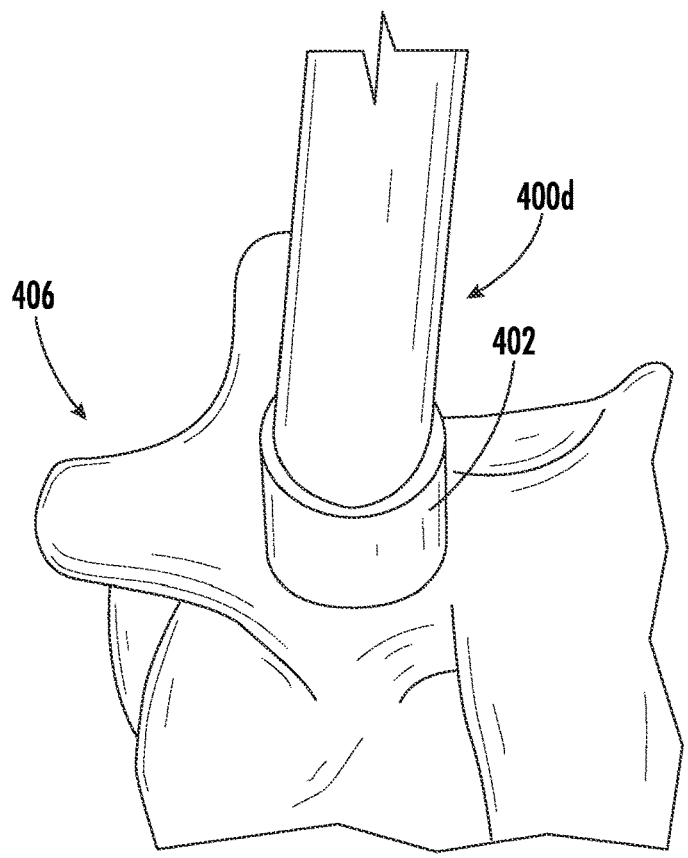
FIG. 14 is a detailed top perspective view of a distal end of the cannula and localized navigation sensor of FIG. 13.
Figure 15:
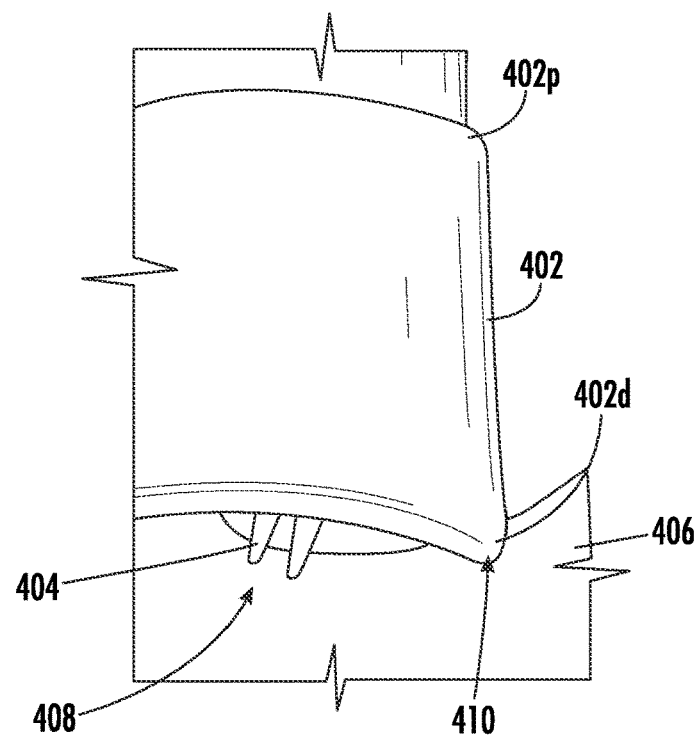
FIG. 15 is a detailed bottom perspective view of the distal end of the cannula and localized navigation sensor of FIG. 13.

FIG. 13 shows one embodiment of a cannula 400 and a localized navigation sensor in the form of a sheath 402 in accordance with the present disclosure. FIGS. 14 and 15 show detailed views of a distal end 402d of the cannula inserted into a surgical site (104). The cannula 400 can have a generally tubular body extending from a proximal end 402p to the distal end 402d, configured for insertion into the surgical site. As described above in connection with the cannula 102 of FIG. 2, the cannula 400 can taper at the distal end and terminate with a plurality of arcuate teeth 404, which can form a distal tip of the cannula and can contact patient anatomy, e.g., vertebral body 406 at the surgical site. The teeth 404 can bite into or otherwise engage the vertebral body 406, which can stabilize the cannula 400 against the bone. The sheath 402, i.e., the localized navigation sensor, and can be coupled to the distal end 400d of the cannula 400. More particularly, a proximal end 402p of the sheath 402 can extend around a circumference of the cannula 400 and can expand radially outwards to a distal end 402d of the sheath. The distal end 402d of the sheath 402 can terminate in-line with the distal tip of the arcuate teeth 404 of the cannula 400, such that the distal tip of the arcuate teeth 404 can be aligned or substantially aligned with the distal end of the sheath. With the cannula 400 inserted into the surgical site such that the arcuate teeth 404 of the cannula can contact the vertebral body 406 at a first location 408, the distal end 402d of the sheath 402 can contact the vertebral body at a second location 410, which can extend along an entire circumference of the sheath's distal end or along a part or parts thereof. The sheath 402 can deflect or deform in response to localized movement of the vertebral body 406. Deflection, deformation, and/or movement of the sheath 402 can be measured, e.g., by one or more resistance-based sensors/resistive element(s) and/or strain gauge(s) as described above, of the sheath 402 and the data can be transmitted to a controller 110 (see FIG. 1) for further processing to detect localized movement.

Figure 16:
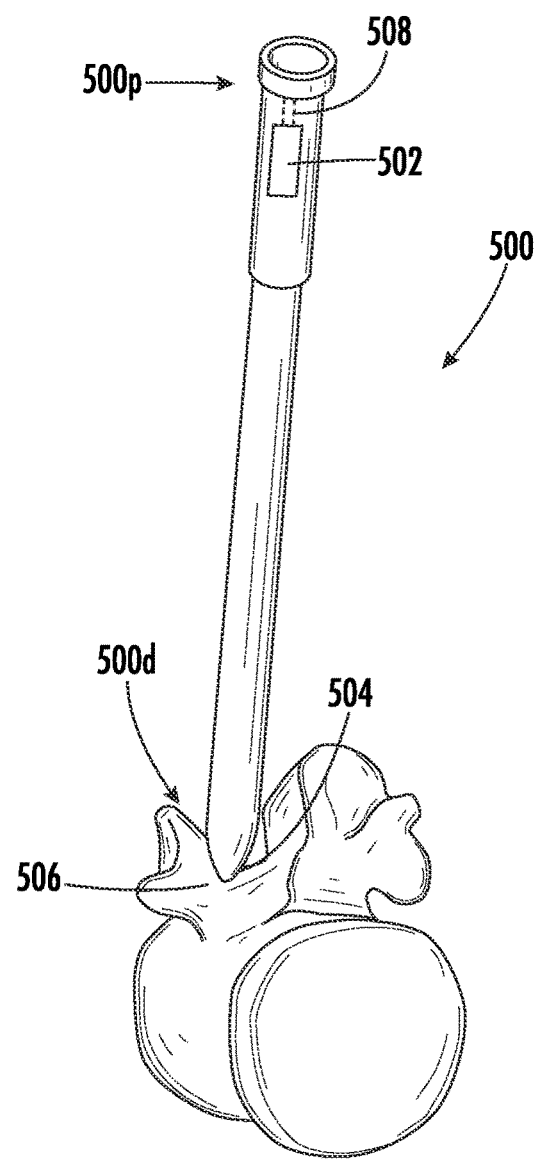
FIG. 16 is an illustration of another embodiment of a cannula and a localized navigation sensor according to the present disclosure placed at a surgical site.
Figure 17:
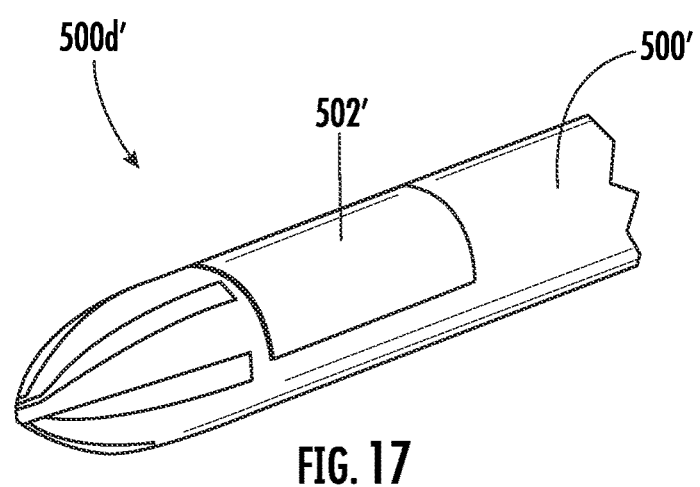
FIG. 17 is a perspective view of an alternative embodiment of the cannula and localized navigation sensor of FIG. 16.

FIG. 16 illustrates another embodiment of a cannula 500 and a localized navigation sensor 502 in accordance with the present disclosure. As discussed in detail below, the localized navigation sensor 502 can generate vibration of the cannula 500 and can be configured to monitor a resonant frequency of the cannula in response to the vibrations. A change in resonant frequency can be detected by the localized navigation sensor 502, which can correspond to localized movement of an anatomic structure at a surgical site. Turning to FIG. 16, the cannula 500 can have a generally tubular body extending between a proximal end 500p and a distal end 500d. The distal end 500d of the cannula 500 can include a plurality of teeth 504 that can contact a pedicle 506, or other anatomic structure. In some embodiments, the localized navigation sensor 502 can be a piezoelectric sensor configured to detect force and/or deflection. In some embodiments, a piezoelectric actuator can be employed that can include an emitter and a receiver, such that the single piezoelectric component can cause a vibration of the cannula 500 and can measure a resonant frequency response. In other embodiments, emitter and receiver components of the localized navigation sensor 502 can be separately coupled to the cannula 500. As shown in FIG. 16, the localized navigation sensor 502 can be mounted or otherwise coupled to the proximal end 500p of the cannula 500. Wires 508 can extend from the localized navigation sensor 502 along the cannula 500 to provide a transmission path for data between the localized navigation sensor and a controller 110 (see FIG. 1). In other embodiments, communication between the localized navigation sensor 502 and the controller can occur through a wireless connection. In some embodiments, a localized navigation sensor 502' can be coupled to a distal end 502d' of a cannula 500', as shown in an alternative embodiment of FIG. 17. By way of non-limiting example, the localized navigation sensor 502, 502' can be a piezo-film vibration sensor produced by TE Connectivity with dimensions of about 25 mm by about 13 mm by about 0.125 mm. Alternative sizes and shapes of the localized navigation sensor 502, 502' fall within the scope of this disclosure and can be determined, at least in part, on the dimensions of the cannula 500, 500'. The localized navigation sensor 502, 502' can be calibrated to establish a baseline resonant frequency measurement each time a surgical instrument is introduced to the surgical site such that changes to the resonant frequency of the cannula 500, 500' can be accurately attributed to localized movement of patient anatomy at the surgical site, rather than introduction of a surgical instrument.

Figure 18A:
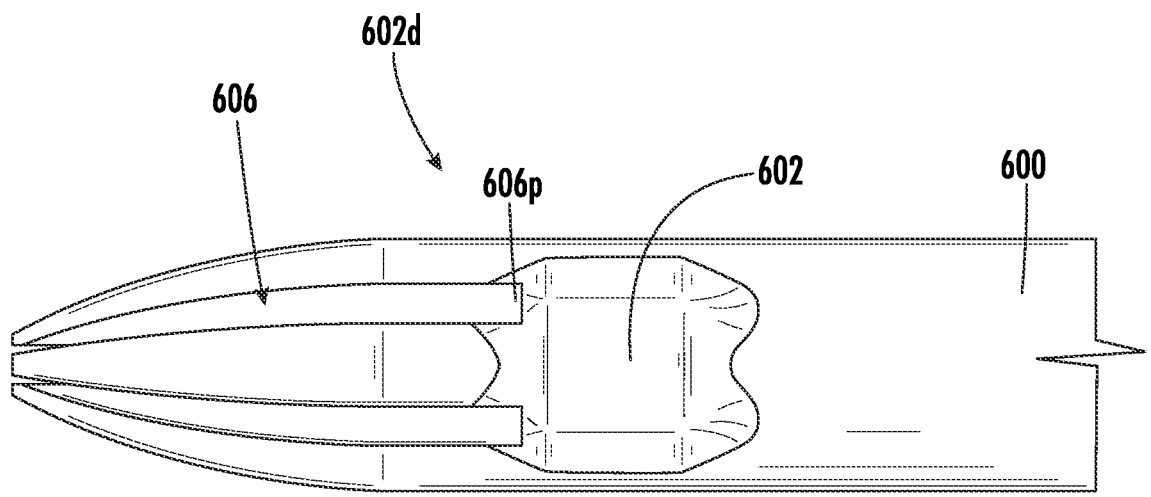
FIG. 18A is a top view of another embodiment of a cannula and a localized navigation sensor according to the present disclosure.
Figure 18B:
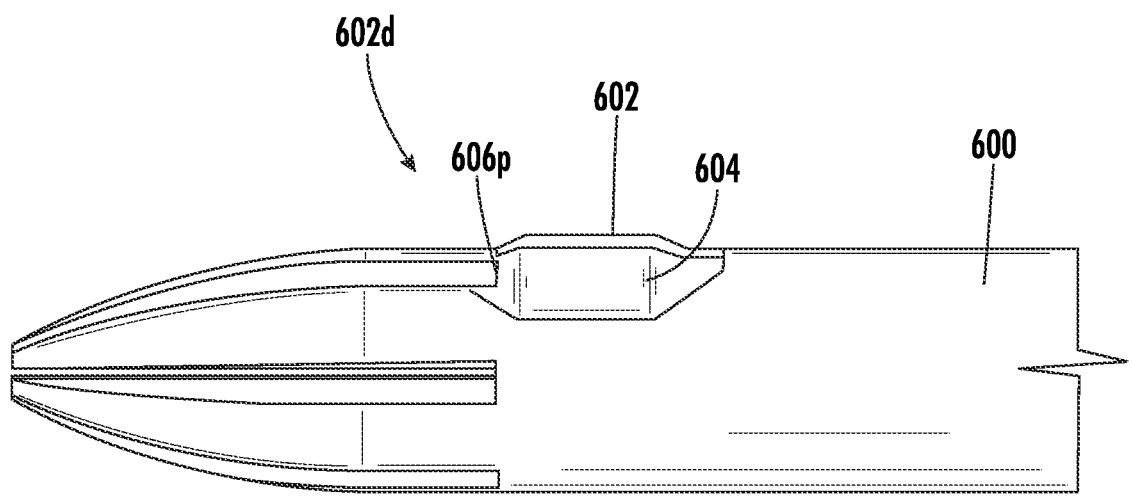
FIG. 18B is a side view of the cannula and localized navigation sensor of FIG. 18A.

FIGS. 18A and 18B illustrate another embodiment of a cannula 600 and a localized navigation sensor 602 in accordance with the present disclosure. Except as described in detail below, the cannula 600 can be similar or substantially similar to the cannulas 102, 202 described above. The localized navigation sensor 602 can be a miniature or micro ultrasound transducer and sensor, which can be used, for example, in a minimally invasive surgical procedure (MIS procedure) in which the ultrasound can measure and monitor position and/or movement of an anatomic structure (e.g., a vertebral body 206, a pedicle 506, etc.) at a surgical site that can be devoid of any airgaps. In other words, the localized navigation sensor 600 can measure and/or monitor the anatomic structure through tissue and/or fluids at the surgical site. In some embodiments, the localized navigation sensor 602 can be embedded into the cannula 600 at a distal end 602d thereof. A protrusion 604 can be formed around the localized navigation sensor 602 such that the sensor can be slightly raised, e.g., up to about 1 mm, off of the surface of the cannula. In some embodiments, the cannula 600 can include a plurality of recesses 606, as described above in connection with FIGS. 4A-4C, and, by way of non-limiting example, the localized navigation sensor 602 can be placed adjacent to a proximal end 606p of one or more of the recesses. In use, the cannula 600 can be inserted into the surgical site 104 (FIG. 1) and brought into proximity of the pedicle 506 (FIG. 16), or other anatomic structure. The cannula 600 can be rotated such that the localized navigation sensor 602 can image or capture a portion of the pedicle 506. A controller 110 (FIG. 1) can then produce and track the image to visualize bone shape of the pedicle and illustrate localized movement thereof. In some embodiments, an ultrasound frequency from the localized navigation sensor 602 can be monitored. Changes in the ultrasound frequency can reflect bone material of the anatomic structure of interest, e.g., the pedicle.

Figure 19:
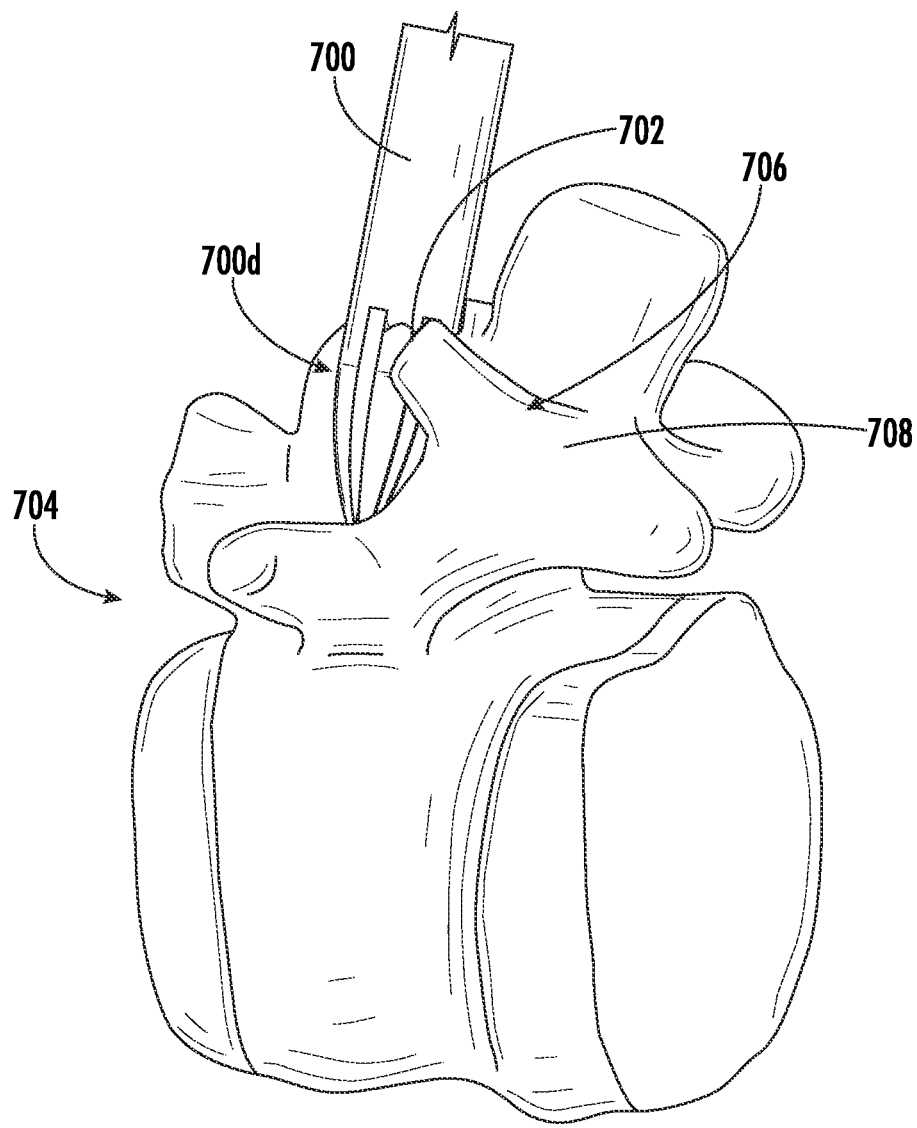
FIG. 19 is an illustration of another embodiment of a cannula and a localized navigation sensor according to the present disclosure placed at a surgical site.

FIG. 19 shows another embodiment of a cannula 700 with a localized navigation sensor 702 coupled to a distal end 700d thereof inserted into a surgical site such that the localized navigation sensor can monitor and detect relative movement of a vertebra 704, or other anatomic structure, at a surgical site 104 (see FIG. 1). Except as described below, the cannula 700 can be similar or identical to any of the cannulas described above. Accordingly, description of the cannula's 700 structure, operation, and use is omitted herein for the sake of brevity. The localized navigation sensor 702 can include one or more micro laser arrays embedded into or otherwise secured to the body of the cannula 700 at the distal end 700d thereof. In one embodiment, with the cannula 700 in proximity to and, in some embodiments, in contact with, the vertebra 704, the localized navigation sensor 702 can perform beam scanning 706 of the vertebra 704, or a portion thereof, without contact between the localized navigation sensor and the vertebra. A controller 110 (see FIG. 1) can receive data from the localized navigation sensor 702 and, leveraging different wavelengths of the data, can create a reconstruction, e.g., a three-dimensional model, of the vertebra 704 and any surrounding structures captured by the beam scanning 706. The localized navigation sensor 702 can continuously scan the vertebra 704 such that localized movement of the vertebra 704 can be detected in the reconstruction by the controller 110. Additionally, or alternatively, the localized navigation sensor 702 can take repeated distance measurements to a single-point or line, e.g., a point or line on a spinous process 708 of the vertebra 704 and can detect localized movement of the spinous process from a change in the distance measurement. In other words, if the facet or spinous process 708 moves relative to the cannula 700, a distance measurement by the localized navigation sensor 702 to a constant single-point or along a constant line will increase or decrease as a function of the movement.

Figure 20:
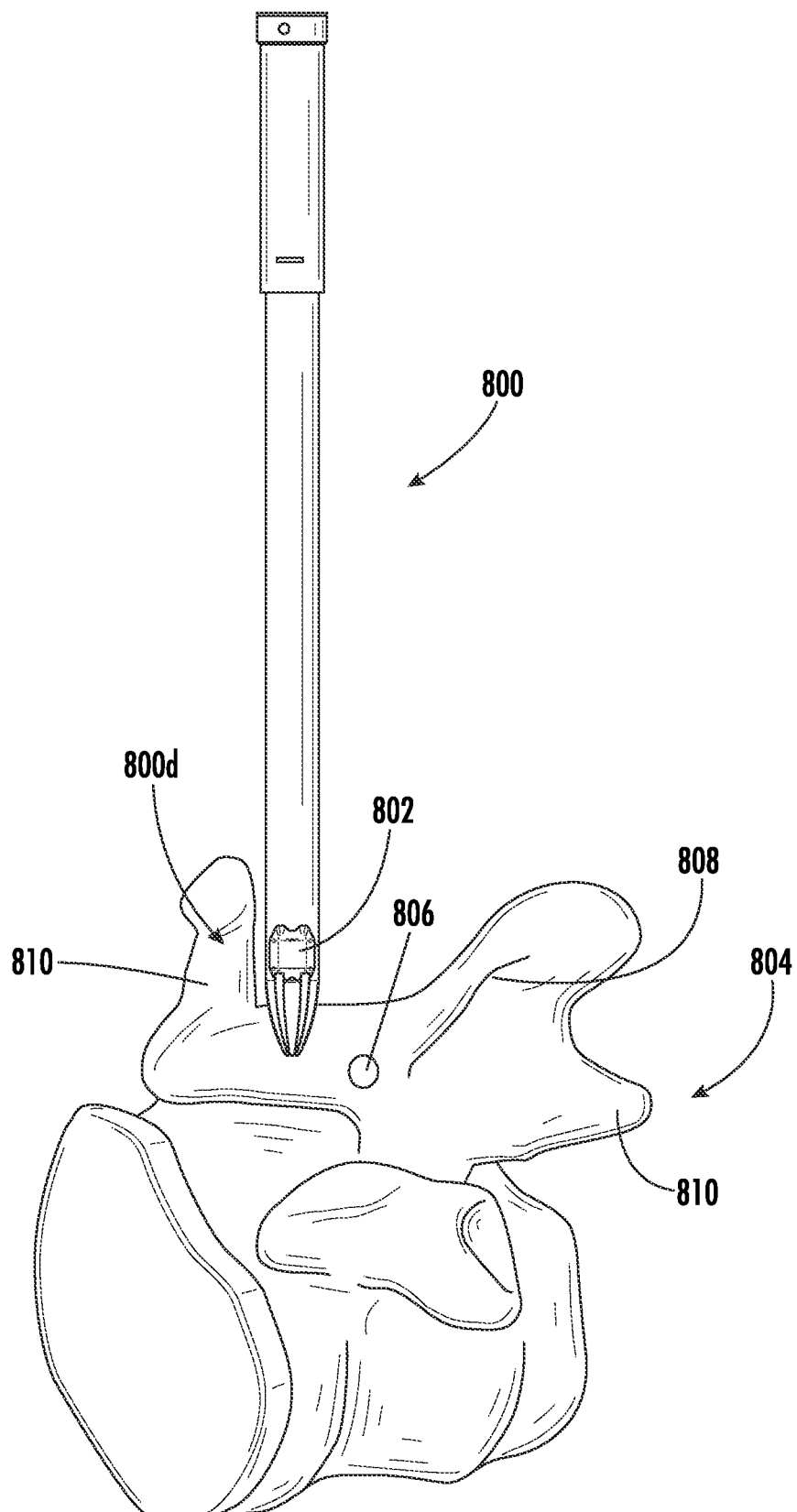
FIG. 20 is an illustration of another embodiment of a cannula and a localized navigation sensor according to the present disclosure placed at a surgical site.

FIG. 20 illustrates another embodiment of a cannula 800 with a localized navigation sensor 802 coupled to a distal end 800d thereof inserted into a surgical site 104 (see FIG. 1) such that the localized navigation sensor can monitor and detect relative movement of a vertebra 804, or other anatomic structure, at the surgical site. Except as described below, the cannula 800 can be similar or identical to any of the cannulas described above. Accordingly, description of the cannula's 800 structure, operation, and use is omitted herein for the sake of brevity. The localized navigation sensor 802 can be an electromagnetic tracker that can measure an electromagnetic field of the surroundings and detect a magnitude of change therein. In one embodiment, one or more electromagnetic sensors 806 can be injected or otherwise placed into the vertebra 804 and can serve as landmarks for the localized navigation sensor 802. In the illustrated embodiment, the electromagnetic sensor 806 can be injected into a base of the spinous process 808, however alternative placement of the electromagnetic sensor can be utilized. By way of non-limiting example, the electromagnetic sensor 806 can be an NDI Micro 6DOF Sensor, with a diameter of about 0.8 mm and a height of about 9 mm. In some embodiments the electromagnetic sensor 806 can be encased in a capsule, e.g., a capsule with a diameter of about 2.8 mm and a height of about 11 mm. With the electromagnetic sensor 806 in place, the localized navigation sensor 802 can monitor the electromagnetic field at close proximity, which can reduce noise in the signal, and can detect localized movement of the vertebra 804 based on unexpected change in the electromagnetic field. In embodiments in which no electromagnetic sensors 806 are placed in the vertebra 804, the localized navigation sensor 802 can monitor an electromagnetic field in proximity to the vertebra once a screw or other metallic hardware (not shown) is placed in the vicinity of the surgical site 104, e.g., a pedicle screw is placed in a pedicle 810 of the vertebra 804 or in a pedicle of an adjacent vertebra. With the metallic hardware in place, the localized navigation sensor 802 can establish a baseline measurement for the electromagnetic field and can detect changes thereto. A significant change in the electromagnetic field can thus be correlated to a change in position of the vertebra 804.

FIG. 21 illustrates one embodiment of a method 1000 of the present disclosure for detecting localized movement of an anatomic structure at a surgical site, which can be performed with any of the systems and devices described herein. In some embodiments, the method 1000 can include alerting a user when detected localized movement exceeds a threshold condition, e.g., as described in connection with box I of FIG. 21. Additionally or alternatively, in some embodiments, the method 1000 can determine whether detected localized movement is recognized or registered by a global navigation system, e.g., as described in connection with box II of FIG. 21. By way of example, the method 1000 is described below with reference to the surgical system 100 of FIG. 1 and the cannula 202 and localized navigation sensor 204 of FIGS. 3-4C, however, any of the systems and devices described herein can be utilized in connection with the method described below.

The method 1000 can include inserting a cannula 202, or other instrument, with a localized navigation sensor 204 coupled thereto into a surgical site 104 (step 1002) and placing the cannula in a desired position for detection of localized movement of a vertebral body 206, or other anatomic structure, at the surgical site (step 1004). This can include, for example, advancing the cannula 202 towards the vertebral body 206 such that a distal end 200*d* of the cannula is in proximity to the vertebral body. More particularly, the cannula 200 can be placed such that the localized navigation sensor 204 coupled to the cannula is brought into a position to collect data upon movement of the vertebral body 206 relative to the cannula 200. For example, one or more tines 208 can be advanced from the distal end 200*d* of the cannula 200 to contact the vertebral body 206. In some embodiments, the cannula 202 can be coupled to a robot arm 108 (see FIG. 1), or other surgical robot device, which can control or assist in controlling movement of the cannula 202 and/or actuation of the localized navigation sensor 204, e.g., extension of the tines 208.

With the cannula 202 placed in the desired position, the localized navigation sensor 204 coupled to the cannula can monitor a position of the vertebral body 206 and detect movement of the vertebral body 206 relative to the cannula (step 1006). More particularly, the localized navigation sensor 204 can collect data, e.g., from sensing element(s) within tines 208 of the sensor that can respond to movement of the vertebral body 206 and transmit the data to a controller 110. The controller 110 can analyze the data from the localized navigation sensor 204 detect a magnitude, change in direction, and/or mode of movement of the vertebral body 206 relative to the cannula. As introduced above, methods in accordance with the present disclosure can sense localized movement of the vertebral body 206 and can determine (i) whether the localized movement exceeds a threshold condition (Box I) and/or (ii) whether the detected localized movement is recognized by a global navigation system 116, 120 (Box II). The localized navigation sensor 204 can transmit data to a controller 110 for further processing and analysis, e.g., to decouple signal transmission from the localized navigation sensor, identify localized movement, etc.

Turning first to embodiments of the method 1000 that can include determining whether localized movement exceeds a threshold condition (Box I), if localized movement is detected at step 1006, the controller 110 can determine whether the detected localized movement exceeds a threshold condition (step 1008). By way of non-limiting example, the controller 110 can determine a magnitude of localized movement of the vertebral body 206 based on the data received from the localized navigation sensor 204 and can compare the detected magnitude of localized movement to a threshold amount of movement, e.g., a pre-determined magnitude of movement that could result in a drill or other tool moving off-target of an intended trajectory (i.e., skiving). By way of further example, in some embodiments, the controller 110 can determine a directional shift of the detected localized movement and compare the directional shift to a threshold condition set of permissible localized movement directions. If the detected localized movement exceeds the threshold condition (e.g., the threshold magnitude of movement, the permissible localized movement directions, etc.) a user can be alerted (step 1010). Alerting the user can include, for example, triggering a visual, auditory, and/or haptic feedback such that a user can be made aware of the exceeded threshold condition. In some embodiments, alerting the user can include logging information in a connected server or computing system. If the detected localized movement does not exceed the threshold condition (step 1008) the surgical procedure can continue (1012). While the surgical procedure continues, the localized navigation sensor 204 can continuously detect localized movement and the method can revert back to step 1006.

If localized movement is detected (step 1006) and a global navigation system 120, 116 is utilized during a surgical procedure, the method 1000 can determine whether detected localized movement is tracked by the global navigation system, i.e., whether the movement of the vertebral body 206 is reflected in the coordinate system established by the global navigation system (step 1014). For example, the controller 110 can receive data from the localized navigation sensor 204 and the global navigation system 120, 116. The controller 110 can compare the detected localized movement, i.e., as determined from the localized navigation sensor data, to the data from the global navigation system regarding placement of the tracked marker(s) and determine whether the detected localized movement of the vertebral body 306 is reflected in the data from the global navigation system. If the detected localized movement of the vertebral body 305 is not tracked by the global navigation system, a user can be alerted (step 1016), which can include any of the alert measures described above with respect to step 1010. The alert issued to the user can signal to the user that there is an increased risk of skiving when a navigated instrument is introduced and/or manipulated at the surgical site resulting from inaccuracy in the global navigation system with respect to placement and/or positioning of the vertebral body 206. On the other hand, if the detected localized movement is tracked by the global navigation system, then the surgical procedure can continue (step 1012). The localized navigation sensor 204 can continuously detect localized movement and the method can revert back to step 1006.

While the steps of determining whether detected localized movement exceeds a threshold condition (1008) and determining whether detected localized movement is reflected in a global coordinate frame (1014) are illustrated in FIG. 21 as separate sub-processes in Box I and Box II, respectively, in some embodiments, systems and methods of the present disclosure can be configured to carry out all of the steps within Box I and Box II. For example, a controller of the present disclosure can be configured to receive data from a localized navigation sensor, determine whether the detected localized movement exceeds a threshold condition (Box I), and determine whether the detected localized movement is reflected in the global coordinate frame (Box II). The steps of Box I and Box II can be carried out simultaneously, sequentially, or individually in response to an instruction command, e.g., that can be pre-programmed into the controller, downloaded from a connected device, input by a user, etc.

Although specific embodiments are described above, changes may be made within the spirit and scope of the concepts described. For example, the above embodiments describe surgical systems and methods of the present disclosure in connection with a surgical procedure of the spine. While this is one contemplated use, the methods and devices of the present disclosure can be equally adapted for use in other areas of a patient's body, e.g., a knee, hip, shoulder, etc. As such, the devices described herein can be formed in a variety of sizes and materials appropriate for use in various areas of a patient's body. Further features and advantages based on the above-described embodiments are also possible and within the scope of the present disclosure. Accordingly, the disclosure is not to be limited by what has been particularly shown and described. All publications and references cited herein are incorporated by reference in the entirety, except for any definitions, subject matter disclaimers or disavowals, and except to the extent that the incorporated material is inconsistent with the express disclosure herein, in which case the language in this disclosure controls.

Examples of the above-described embodiments can include the following:

The invention claimed is:

1. A surgical system, comprising:
   a robot arm;
   a cannula coupled to the robot arm;
   a localized navigation sensor coupled to a distal end of the cannula and configured to detect movement of an anatomic structure relative to the cannula; and
   a controller configured to:
      receive data from the localized navigation sensor;
      receive data from a global navigation system that tracks a location of a navigation marker located remotely from the anatomic structure; and
      determine if movement of the anatomic structure detected by the localized navigation sensor is tracked by the global navigation system.

2. The system of claim 1, wherein the localized navigation sensor is configured to detect a magnitude and a direction of localized movement of the anatomic structure.

3. The system of claim 1, wherein the localized navigation sensor extends from the distal end of the cannula.

4. The system of claim 1, wherein the localized navigation sensor includes a plurality of tines configured to extend distally from the distal end of the cannula.

5. The system of claim 1, wherein the localized navigation sensor includes at least one tine configured to extend radially from the distal end of the cannula.

6. The system of claim 1, wherein the localized navigation sensor includes at least one tine configured to extend from the distal end of the cannula, and
   wherein the controller is further configured to determine movement of the anatomic structure based on a change in one or more of a geometry of the at least one tine and a location of the at least one tine.

7. The system of claim 1, wherein the localized navigation sensor comprises at least one of the following: a piezoelectric actuator, a piezoelectric sensor, an ultrasound sensor, an electromagnetic sensor, a laser, a resistance-based sensor, or a strain gauge.

8. The system of claim 1, wherein the anatomic structure is a vertebral body.

9. A surgical method, comprising:
   positioning a cannula relative to an anatomic structure using a robot arm;
   detecting movement of the anatomic structure relative to the cannula using a localized navigation sensor coupled to a distal end of the cannula; and
   determining if movement of the anatomic structure detected by the localized navigation sensor is tracked by a global navigation system that tracks a location of a navigation marker located remotely from the anatomic structure.

10. The method of claim 9, wherein the localized navigation sensor includes at least one tine, the method further comprising extending the at least one tine from the distal end of the cannula to contact the anatomic structure.

11. The method of claim 10, wherein detecting the movement of the anatomic structure further comprises measuring at least one of a deformation in the tine or a change in location of the tine.

12. The method of claim 9, further comprising determining if movement of the anatomic structure exceeds a threshold amount of movement.

13. The method of claim 9, further comprising alerting a user when the movement of the anatomic structure is not tracked by the global navigation system.

14. The method of claim 9, wherein the anatomic structure is a vertebral body.

15. A surgical system, comprising:
   a cannula coupled to a robot arm;
   a localized navigation sensor comprising one or more tines, the localized navigation sensor coupled to a distal end of the cannula and configured to detect movement of an anatomic structure relative to the cannula; and
   a controller configured to:
      receive data from the localized navigation sensor indicating movement of the anatomic structure relative to the cannula;
      receive data from a global navigation system;
      determine if movement of the anatomic structure detected by the localized navigation sensor is tracked by the global navigation system; and
      if the movement of the anatomic structure detected by the localized navigation sensor is not tracked by the global navigation system, generate an alert.

16. The system of claim 15, wherein the alert comprises an indication that there is an increased risk of skiving.

17. The system of claim 16, wherein the controller is further configured to determine if movement of the anatomic structure detected by the localized navigation sensor exceeds a threshold.

18. The system of claim 17, wherein the threshold is a magnitude.

19. The system of claim 17, wherein the threshold is a direction.

20. The system of claim 17, wherein, if the movement of the anatomic structure detected by the localized navigation sensor exceeds the threshold, the controller is further configured to generate an alert.

* * * * *